United States Patent
Yeung et al.

(10) Patent No.: US 11,578,054 B2
(45) Date of Patent: Feb. 14, 2023

(54) COMPOUNDS USEFUL AS IMMUNOMODULATORS

(71) Applicant: Bristol-Myers Squibb Company, Princeton, NJ (US)

(72) Inventors: Kap-Sun Yeung, Madison, CT (US); Denis R. St. Laurent, Newington, CT (US); David R. Langley, Meriden, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 233 days.

(21) Appl. No.: 16/977,374

(22) PCT Filed: Feb. 28, 2019

(86) PCT No.: PCT/US2019/020032
§ 371 (c)(1),
(2) Date: Sep. 1, 2020

(87) PCT Pub. No.: WO2019/169123
PCT Pub. Date: Sep. 6, 2019

(65) Prior Publication Data
US 2021/0094932 A1 Apr. 1, 2021

Related U.S. Application Data

(60) Provisional application No. 62/637,009, filed on Mar. 1, 2018.

(51) Int. Cl.
*C07D 213/85* (2006.01)
*C07D 401/12* (2006.01)
*C07D 401/14* (2006.01)

(52) U.S. Cl.
CPC ......... *C07D 401/12* (2013.01); *C07D 213/85* (2013.01); *C07D 401/14* (2013.01)

(58) Field of Classification Search
CPC ... C07D 213/85; C07D 401/12; C07D 401/14
See application file for complete search history.

(56) References Cited

U.S. PATENT DOCUMENTS

| | | | |
|---|---|---|---|
| 9,850,225 B2 | 12/2017 | Chupak et al. | |
| 9,872,852 B2 | 1/2018 | Chupak et al. | |
| 10,144,706 B2 | 12/2018 | Yeung et al. | |
| 10,590,105 B2 | 3/2020 | Yeung et al. | |
| 10,745,382 B2 | 8/2020 | Yeung et al. | |
| 10,882,844 B2 | 1/2021 | Yeung et al. | |
| 10,919,852 B2 * | 2/2021 | Lange | C07D 403/12 |
| 11,046,675 B2 | 6/2021 | Yeung et al. | |

FOREIGN PATENT DOCUMENTS

| | | |
|---|---|---|
| EP | 2011788 A1 | 1/2009 |
| WO | WO 2015034820 A1 | 3/2015 |
| WO | WO 2015160641 A2 | 10/2015 |
| WO | WO 2017066227 A1 | 4/2017 |
| WO | WO 2018005374 A1 | 1/2018 |
| WO | WO 2018009505 A1 | 1/2018 |
| WO | WO 2018044963 A1 | 3/2018 |
| WO | WO 2018118848 A1 | 6/2018 |
| WO | WO 2018183171 A1 | 10/2018 |
| WO | WO 2019023575 A1 | 1/2019 |
| WO | WO 2019147662 A1 | 8/2019 |

OTHER PUBLICATIONS

Guzik, K., et al., "Small-Molecule Inhibitors of the Programmed Cell Death-1/Programmed Death-Ligand 1 (PD-1/PD-L1) Interaction via Transiently Induced Protein States and Dimerization of PD-L1," *Journal of Medicinal Chemistry*, 60(13):5857-5867, American Chemical Society, United States (Jul. 2017).

\* cited by examiner

*Primary Examiner* — Laura L Stockton
(74) *Attorney, Agent, or Firm* — Sterne, Kessler, Goldstein & Fox P.L.L.C.

(57) ABSTRACT

The present disclosure generally relates to compounds useful as immunomodulators. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

13 Claims, No Drawings
Specification includes a Sequence Listing.

SEQUENCE LISTING

<160> NUMBER OF SEQ ID NOS: 2

<210> SEQ ID NO 1
<211> LENGTH: 384
<212> TYPE: PRT
<213> ORGANISM: Artificial Sequence
<220> FEATURE:
<223> OTHER INFORMATION: hPD1(25-167)-3S-IG

<400> SEQUENCE: 1

| | | | | | | | | | | | | | | |
|---|---|---|---|---|---|---|---|---|---|---|---|---|---|---|
| Leu | Asp | Ser | Pro | Asp | Arg | Pro | Trp | Asn | Pro | Thr | Phe | Ser | Pro | Ala |
| 1 | | | | 5 | | | | | 10 | | | | | 15 |
| Leu | Leu | Val | Val | Thr | Glu | Gly | Asp | Asn | Ala | Thr | Phe | Thr | Cys | Ser | Phe |
| | | | 20 | | | | | 25 | | | | | 30 | |
| Ser | Asn | Thr | Ser | Glu | Ser | Phe | Val | Leu | Asn | Trp | Tyr | Arg | Met | Ser | Pro |
| | | | 35 | | | | | 40 | | | | | 45 | |
| Ser | Asn | Gln | Thr | Asp | Lys | Leu | Ala | Ala | Phe | Pro | Glu | Asp | Arg | Ser | Gln |
| | 50 | | | | | 55 | | | | | 60 | | | | |
| Pro | Gly | Gln | Asp | Cys | Arg | Phe | Arg | Met | Thr | Gln | Leu | Pro | Asn | Gly | Arg |
| 65 | | | | | 70 | | | | | 75 | | | | | 80 |
| Asp | Phe | His | Met | Ser | Val | Val | Arg | Ala | Arg | Arg | Asn | Asp | Ser | Gly | Thr |
| | | | | 85 | | | | | 90 | | | | | 95 | |
| Tyr | Leu | Cys | Gly | Ala | Ile | Ser | Leu | Ala | Pro | Lys | Ala | Gln | Ile | Lys | Glu |
| | | | 100 | | | | | 105 | | | | | 110 | | |
| Ser | Leu | Arg | Ala | Glu | Leu | Arg | Val | Thr | Glu | Arg | Arg | Ala | Glu | Val | Pro |
| | | | 115 | | | | | 120 | | | | | 125 | | |
| Thr | Ala | His | Pro | Ser | Pro | Ser | Pro | Arg | Pro | Ala | Gly | Gln | Phe | Gln | Gly |
| | | 130 | | | | | 135 | | | | | 140 | | | |
| Ser | Pro | Gly | Gly | Gly | Gly | Gly | Arg | Glu | Pro | Lys | Ser | Ser | Asp | Lys | Thr |
| 145 | | | | | 150 | | | | | 155 | | | | | 160 |
| His | Thr | Ser | Pro | Pro | Ser | Pro | Ala | Pro | Glu | Leu | Leu | Gly | Gly | Ser | Ser |
| | | | | 165 | | | | | 170 | | | | | 175 | |
| Val | Phe | Leu | Phe | Pro | Pro | Lys | Pro | Lys | Asp | Thr | Leu | Met | Ile | Ser | Arg |
| | | | 180 | | | | | 185 | | | | | 190 | | |
| Thr | Pro | Glu | Val | Thr | Cys | Val | Val | Val | Asp | Val | Ser | His | Glu | Asp | Pro |
| | | | 195 | | | | | 200 | | | | | 205 | | |
| Glu | Val | Lys | Phe | Asn | Trp | Tyr | Val | Asp | Gly | Val | Glu | Val | His | Asn | Ala |
| | 210 | | | | | 215 | | | | | 220 | | | | |
| Lys | Thr | Lys | Pro | Arg | Glu | Glu | Gln | Tyr | Asn | Ser | Thr | Tyr | Arg | Val | Val |
| 225 | | | | | 230 | | | | | 235 | | | | | 240 |
| Ser | Val | Leu | Thr | Val | Leu | His | Gln | Asp | Trp | Leu | Val | Gly | Lys | Glu | Tyr |
| | | | | 245 | | | | | 250 | | | | | 255 | |
| Lys | Cys | Lys | Val | Ser | Asn | Lys | Ala | Leu | Pro | Ala | Pro | Ile | Glu | Lys | Thr |
| | | | 260 | | | | | 265 | | | | | 270 | | |
| Ile | Ser | Lys | Ala | Lys | Gly | Gln | Pro | Arg | Glu | Pro | Gln | Val | Tyr | Thr | Leu |
| | | 275 | | | | | 280 | | | | | 285 | | | |
| Pro | Pro | Ser | Arg | Asp | Glu | Leu | Thr | Lys | Asn | Gln | Val | Ser | Leu | Thr | Cys |
| | 290 | | | | | 295 | | | | | 300 | | | | |
| Leu | Val | Lys | Gly | Phe | Tyr | Pro | Ser | Asp | Ile | Ala | Val | Glu | Trp | Glu | Ser |
| 305 | | | | | 310 | | | | | 315 | | | | | 320 |
| Asn | Gly | Gln | Pro | Glu | Asn | Asn | Tyr | Lys | Thr | Thr | Pro | Pro | Val | Leu | Asp |
| | | | | 325 | | | | | 330 | | | | | 335 | |
| Ser | Asp | Gly | Ser | Phe | Phe | Leu | Tyr | Ser | Lys | Leu | Thr | Val | Asp | Lys | Ser |
| | | | 340 | | | | | 345 | | | | | 350 | | |
| Arg | Trp | Gln | Gln | Gly | Asn | Val | Phe | Ser | Cys | Ser | Val | Met | His | Glu | Ala |

```
                    355                 360                 365
Leu His Asn His Tyr Thr Gln Lys Ser Leu Ser Leu Ser Pro Gly Lys
        370                 375                 380

<210> SEQ ID NO 2
<211> LENGTH: 238
<212> TYPE: PRT
<213> ORGANISM: Artificial Sequence
<220> FEATURE:
<223> OTHER INFORMATION: hPDL1(18-239)-TVMV-His

<400> SEQUENCE: 2

Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110

Val Asn Ala Pro Tyr Asn Lys Ile Asn Gln Arg Ile Leu Val Val Asp
        115                 120                 125

Pro Val Thr Ser Glu His Glu Leu Thr Cys Gln Ala Glu Gly Tyr Pro
    130                 135                 140

Lys Ala Glu Val Ile Trp Thr Ser Ser Asp His Gln Val Leu Ser Gly
145                 150                 155                 160

Lys Thr Thr Thr Thr Asn Ser Lys Arg Glu Glu Lys Leu Phe Asn Val
                165                 170                 175

Thr Ser Thr Leu Arg Ile Asn Thr Thr Thr Asn Glu Ile Phe Tyr Cys
            180                 185                 190

Thr Phe Arg Arg Leu Asp Pro Glu Glu Asn His Thr Ala Glu Leu Val
        195                 200                 205

Ile Pro Glu Leu Pro Leu Ala His Pro Pro Asn Glu Arg Thr Gly Ser
    210                 215                 220

Ser Glu Thr Val Arg Phe Gln Gly His His His His His His
225                 230                 235
```

COMPOUNDS USEFUL AS IMMUNOMODULATORS

The present disclosure generally relates to compounds useful as inhibitors of the PD-1/PD-L1 protein/protein and CD80/PD-L1 protein/protein interactions. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC) (Sharpe et al., Nat. Imm. 2007). When PD-1 expressing T cells contact cells expressing its ligands, functional activities in response to antigenic stimuli, including proliferation, cytokine secretion, and cytolytic activity are reduced. PD-1/PD-Ligand interactions down regulate immune responses during resolution of an infection or tumor, or during the development of self tolerance (Keir Me, Butte M J, Freeman G J, et al. *Annu. Rev. Immunol.* 2008; 26: Epub). Chronic antigen stimulation, such as that which occurs during tumor disease or chronic infections, results in T cells that express elevated levels of PD-1 and are dysfunctional with respect to activity towards the chronic antigen (reviewed in Kim and Ahmed, Curr Opin Imm, 2010). This is termed "T cell exhaustion". B cells also display PD-1/PD-ligand suppression and "exhaustion".

PD-L1 has also been shown to interact with CD80 (Butte M J et al., *Immunity* 27:111-122 (2007)). The interaction of PD-L1/CD80 on expressing immune cells has been shown to be an inhibitory one. Blockade of this interaction has been shown to abrogate this inhibitory interaction (Paterson A M, et al., *J Immunol.*, 187:1097-1105 (2011); Yang J, et al. *J Immunol.* August 1; 187(3):1113-9 (2011)).

Blockade of the PD-1/PD-L1 interaction using antibodies to PD-L1 has been shown to restore and augment T cell activation in many systems. Patients with advanced cancer benefit from therapy with a monoclonal antibody to PD-L1 (Brahmer et al., *New Engl J Med* 2012). Preclinical animal models of tumors have shown that blockade of the PD-1/PD-L1 pathway by monoclonal antibodies can enhance the immune response and result in the immune response to a number of histologically distinct tumors (Dong H, Chen L. *J Mol Med.* 2003; 81(5):281-287; Dong H, Strome S E, Salamoa D R, et al. *Nat Med.* 2002; 8(8):793-800).

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1 (Barber D L, Wherry E J, Masopust D, et al. *Nature* 2006; 439(7077):682-687). Humanized mice infected with HIV-1 show enhanced protection against viremia and reduced viral depletion of CD4+ T cells (Palmer et al., *J. Immunol* 2013). Blockade of PD-1/PD-L1 through monoclonal antibodies to PD-L1 can restore in vitro antigen-specific functionality to T cells from HIV patients (Day, *Nature* 2006; Petrovas, *J. Exp. Med.* 2006; Trautman, *Nature Med.* 2006; D'Souza, *J. Immunol.* 2007; Zhang, *Blood* 2007; Kaufmann, *Nature Imm.* 2007; Kasu, *J. Immunol.* 2010; Porichis, *Blood* 2011), HCV patients [Golden-Mason, *J. Virol.* 2007; Jeung, J. Leuk. *Biol.* 2007; Urbani, *J. Hepatol.* 2008; Nakamoto, *PLoS Path.* 2009; Nakamoto, *Gastroenterology* 2008] or HBV patients (Boni, *J. Virol.* 2007; Fisicaro, *Gastro.* 2010; Fisicaro et al., *Gastroenterology,* 2012; Boni et al., *Gastro.,* 2012; Penna et al., *J Hep,* 2012; Raziorrough, *Hepatology* 2009; Liang, *World J Gastro.* 2010; Zhang, *Gastro.* 2008).

Blockade of the PD-L1/CD80 interaction has also been shown to stimulate immunity (Yang J., et al., *J Immunol.* August 1; 187(3):1113-9 (2011)). The immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., *Nat Rev Immunol* (2013)). These include increased levels of PD-1 and PD-L1 and T ceoll apoptosis (Guignant, et al, *Crit. Care* (2011)). Antibodies directed to PD-L1 can reduce the level of Immune cell apoptosis (Zhang et al, *Crit. Care* (2011)). Furthermore, mice lacking PD-1 expression are more resistant to septic shock symptoms than wildtype mice (Yang J., et al. *J Immunol.* August 1; 187(3):1113-9 (2011)). Studies have revealed that blockade of the interactions of PD-L1 using antibodies can suppress inappropriate immune responses and ameliorate disease symptoms.

In addition to enhancing immunologic responses to chronic antigens, blockade of the PD-1/PD-L1 pathway has also been shown to enhance responses to vaccination, including therapeutic vaccination in the context of chronic infection (S. J. Ha, S. N. Mueller, E. J. Wherry et al., *The Journal of Experimental Medicine*, vol. 205, no. 3, pp. 543-555, 2008.; A. C. Finnefrock, A. Tang, F. Li et al., *The Journal of Immunology*, vol. 182, no. 2, pp. 980-987, 2009; M. -Y. Song, S. -H. Park, H. J. Nam, D. -H. Choi, and Y.-C. Sung, The Journal of Immunotherapy, vol. 34, no. 3, pp. 297-306, 2011).

The PD-1 pathway is a key inhibitory molecule in T cell exhaustion that arises from chronic antigen stimulation during chronic infections and tumor disease. Blockade of the PD-1/PD-L1 interaction through targeting the PD-L1 protein has been shown to restore antigen-specific T cell immune functions in vitro and in vivo, including enhanced responses to vaccination in the setting of tumor or chronic infection.

Accordingly, agents that block the interaction of PD-L1 with either PD-1 or CD80 are desired.

Applicants found potent compounds that have activity as inhibitors of the interaction of PD-L1 with PD-1 and CD80, and thus may be useful for therapeutic administration to enhance immunity in cancer or infections, including therapeutic vaccine. These compounds are provided to be useful as pharmaceuticals with desirable stability, bioavailability, therapeutic index, and toxicity values that are important to their drugability.

In a first aspect the present disclosure provides a compound of formula (I)

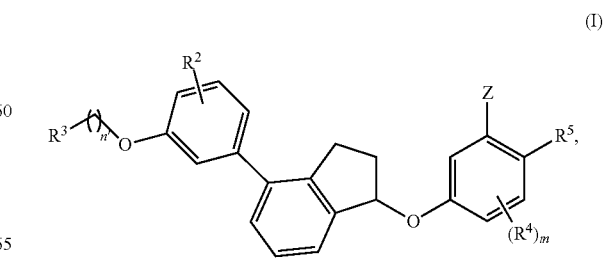

or a pharmaceutically acceptable salt thereof, wherein:
m is 0, 1, or 2;
n' is 1, 2, or 3;
Z is selected from hydrogen, —$CH_3$, —$O(CH_2)_nX$ and —$O(CH_2)_nAr$; wherein
n is 1, 2, 3, or 4;
X is selected from hydrogen, —$CH_3$, —$CF_3$, CN, —$CO_2R'$, —$C(O)NH_2$, $OR^1$, and pyrrolidonyl;
$R^1$ is H or $C_1$-$C_3$alkyl, provided that when n is 1, $R^1$ is $C_1$-$C_3$alkyl;
Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from $C_1$-$C_4$alkoxy, $C_1$-$C_4$alkoxycarbonyl, $C_1$-$C_4$alkoxycarbonylamino, $C_1$-$C_4$alkyl, ($C_1$-$C_4$alkyl)carbonyl, ($C_1$-$C_4$alkyl)sulfonyl, amido, aminocarbonyl, aminocarbonyl($C_1$-$C_3$alkyl), —$(CH_2)_qCO_2C_1$-$C_4$alkyl, —$(CH_2)_qOH$, carboxy, cyano, formyl, halo, halo$C_1$-$C_4$alkyl, halo$C_1$-$C_4$alkoxy, nitro, phenyl optionally substituted with one cyano group, phenyloxy optionally substituted with one halo group, phenylcarbonyl, pyrrole, and tetrahydropyran; and wherein q is 0, 1, 2, 3, or 4;
$R^2$ is selected from hydrogen, $C_1$-$C_3$alkyl, cyano, halo, and halo$C_1$-$C_3$alkyl;
$R^3$ is selected from

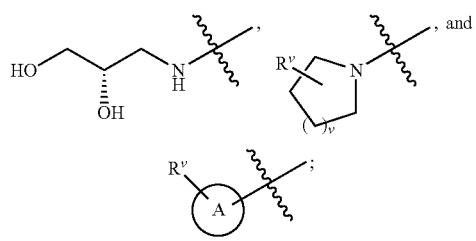

wherein
v is 1 or 2;
ring A is a five- or six-membered ring containing one nitrogen atom wherein said ring is attached to the parent molecular moiety through a carbon atom in the ring; and
$R^v$ is selected to $C_1$-$C_3$alkyl, $C_1$-$C_3$alkylcarbonylamino, and hydroxy;
provided that when $R^3$ is

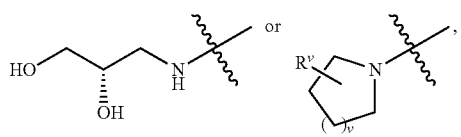

then n' is 2 or 3;
each $R^4$ is independently selected from $C_2$-$C_4$alkenyl, $C_1$-$C_4$alkoxy, $C_1$-$C_4$alkyl, cyano, halo, and halo$C_1$-$C_4$alkyl; and
$R^5$ is selected from —$(CH_2)_pCHO$, —$(CH_2)_pCO_2H$, —$(CH_2)_wOH$, —$C(O)NR^{100}R^{101}$, —$CH(CH_3)NR^qR^8$, and —$(CH_2)_wNR^qR^8$; wherein
$R^{100}$ and $R^{101}$ are selected from hydrogen, $C_1$-$C_6$alkyl, and hydroxy($C_1$-$C_6$alkyl) optionally substituted with an additional hydroxy group; or, $R^{100}$ and $R^{101}$, together with the nitrogen atom to which they are attached, form a six-membered ring optionally substituted with a carboxy group;
p is 0, 1, 2, or 3;
w is 1, 2, 3, or 4;
$R^q$ is selected from hydrogen, $C_1$-$C_4$alkyl, benzyl, ($C_3$-$C_6$cycloalkyl)$C_1$-$C_3$alkyl, halo$C_1$-$C_4$alkyl, hydroxy$C_1$-$C_6$alkyl optionally substituted with a second hydroxy group, and pyridinyl($C_1$-$C_3$alkyl) optionally substituted with a cyano group; and
$R^8$ is selected from hydrogen, $C_1$-$C_4$alkyl, —$(CH_2)_nN(CH_3)_2$, carboxy$C_2$-$C_6$alkenyl, carboxy$C_1$-$C_6$alkyl, and hydroxy$C_1$-$C_6$alkyl, wherein the alkyl part of the carboxy$C_1$-$C_6$alkyl and the hydroxy$C_1$-$C_6$alkyl is optionally substituted with one hydroxy or phenyl group wherein the phenyl group is further optionally substituted with a hydroxy group;

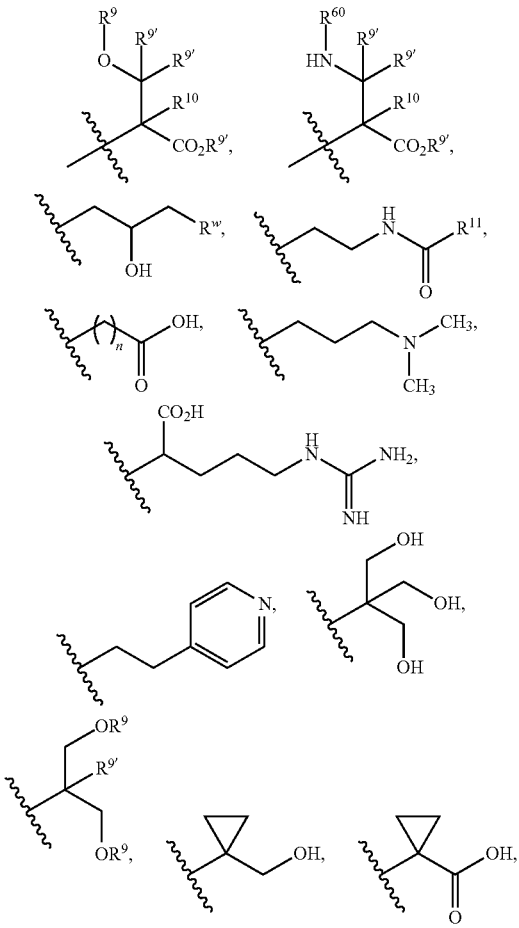

and
$R^w$ is —$CONH_2$,
$R^9$ is selected from hydrogen, benzyl, and methyl;
each $R^{9'}$ is independently selected from hydrogen and $C_1$-$C_3$alkyl;
$R^{10}$ is selected from hydrogen, $C_1$-$C_3$alkyl, and benzyl;
$R^{11}$ is selected from $C_2$-$C_4$alkenyl and $C_1$-$C_4$alkyl; and
$R^{60}$ is selected from hydrogen, $C_1$-$C_6$alkyl, and $C_1$-$C_6$alkoxycarbonyl,
or
$R^8$ and $R^q$, together with the nitrogen atom to which they are attached, form a ring selected from

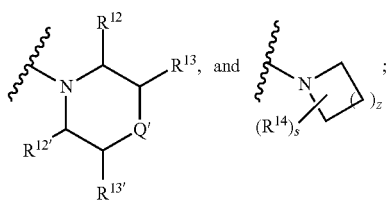

wherein
s is 0, 1, or 2;
z is 1, 2, or 3;
Q' is selected from CHR$^{13''}$, S, O, NH, NC(O)OC$_1$-C$_6$alkyl, N(CH$_2$)$_2$OH, and NCH$_3$;
R$^{12}$ and R$^{12'}$ are independently selected from hydrogen, —CO$_2$H, hydroxyC$_1$-C$_4$alkyl, oxo, and —C(O)NHSO$_2$R$^{16}$;
R$^{13}$ and R$^{13'}$ are independently selected from hydrogen, hydroxyC$_1$-C$_4$alkyl, oxo, and —CO$_2$H;
R$^{13''}$ is selected from hydroxyC$_1$-C$_3$alkyl, and —CO$_2$H;
each R$^{41}$ is independently selected from C$_1$-C$_4$alkoxycarbonyl, carboxy, halo, hydroxy, hydroxyC$_1$-C$_4$alkyl, —NR$^{c'}$R$^{d'}$, and phenyloxycarbonyl wherein the phenyl is optionally substituted with a nitro group, wherein R$^{c'}$ and R$^{d'}$ are independently selected from hydrogen, C$_1$-C$_4$alkoxycarbonyl, and C$_1$-C$_4$alkylcarbonyl; and
R$^{16}$ is selected from trifluoromethyl, cyclopropyl, C$_1$-C$_4$alkyl, dimethylamino, and imidazolyl substituted with a methyl group.

In a first embodiment of the first aspect, the present disclosure provides a compound of formula (I), or a pharmaceutically acceptable salt thereof, wherein R$^3$ is selected from

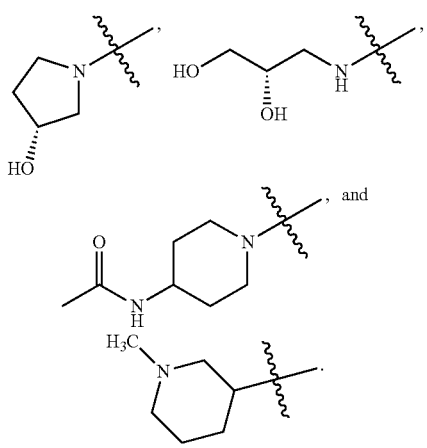

In a second embodiment of the first aspect, the present disclosure provides a compound of formula (I), or a pharmaceutically acceptable salt thereof, wherein R$^3$ is

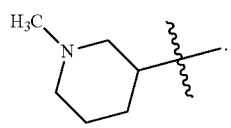

In a third embodiment of the first aspect, the present disclosure provides a compound of formula (I), or a pharmaceutically acceptable salt thereof, wherein R$^2$ is halo.

In a fourth embodiment of the first aspect, the present disclosure provides a compound of formula (I), or a pharmaceutically acceptable salt thereof, wherein Z is —O(CH$_2$)$_n$Ar wherein n is 1 and Ar is pyridinyl substituted with one cyano group.

In a fifth embodiment of the first aspect, the present disclosure provides a compound of formula (I), or a pharmaceutically acceptable salt thereof, wherein m is 1 and R$^4$ is halo.

In a sixth embodiment of the first aspect, the present disclosure provides a compound of formula (I), or a pharmaceutically acceptable salt thereof, wherein R$^5$ is

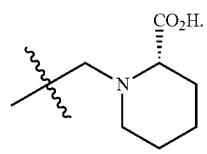

In a seventh embodiment of the first aspect, the present disclosure provides a compound of formula (I), or a pharmaceutically acceptable salt thereof, wherein R$^5$ is

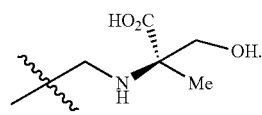 [SMILES: *CN[C@](C)(CO)C(=O)O]

In an eighth embodiment of the first aspect, the present disclosure provides a compound of formula (I), or a pharmaceutically acceptable salt thereof, wherein R$^5$ is —CH$_2$OH.

In an ninth embodiment of the first aspect, the present disclosure provides a compound of formula (I), or a pharmaceutically acceptable salt thereof, wherein R$^5$ is

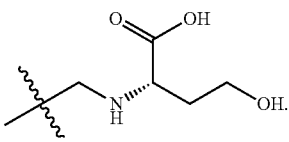 [SMILES: *CN[C@@H](CCO)C(=O)O]

In a tenth embodiment of the first aspect, the present disclosure provides a compound of formula (I), or a pharmaceutically acceptable salt thereof, wherein:
Z is —O(CH$_2$)$_n$Ar wherein n is 1 and Ar is pyridinyl substituted with one cyano group;
R$^2$ is halo;
R$^3$ is selected from

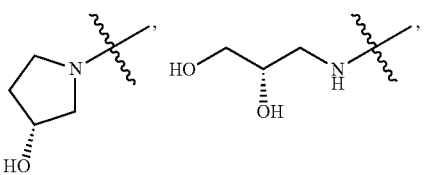

-continued

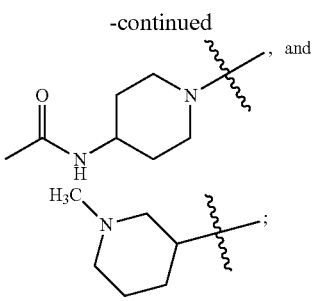
, and m is 1;
R⁴ is halo; and
R⁵ is selected from

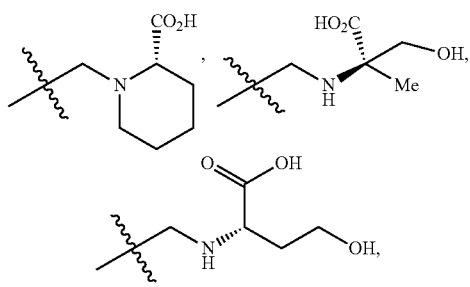

and —CH₂OH.

In a second aspect, the present disclosure provides a pharmaceutical composition comprising a compound of formula (I), or a pharmaceutically acceptable salt thereof, and a pharmaceutically acceptable carrier.

In a third aspect, the present disclosure provides a method of enhancing, stimulating, modulating and/or increasing the immune response in a subject in need thereof, said method comprising administering to the subject a therapeutically effective amount of a compound of formula (I), or a pharmaceutically acceptable salt thereof. In a first embodiment of the third aspect, the method further comprises administering an additional agent prior to, after, or simultaneously with the compound of formula (I), or the pharmaceutically acceptable salt thereof. In a second embodiment, the additional agent is an antimicrobial agent, an antiviral agent, a cytotoxic agent, a gene expression modulatory agent, and/or an immune response modifier.

In a fourth aspect, the present disclosure provides a method of inhibiting growth, proliferation, or metastasis of cancer cells in a subject in need thereof, said method comprising administering to the subject a therapeutically effective amount of a compound of formula (I), or a pharmaceutically acceptable salt. In a first embodiment of the fourth aspect, the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

In a fifth aspect, the present disclosure provides a method of treating an infectious disease in a subject in need thereof, the method comprising administering to the subject a therapeutically effective amount of a compound of formula (I), or a pharmaceutically acceptable salt thereof. In a first embodiment of the fifth aspect, the infectious disease is caused by a virus. In a second embodiment of the fifth aspect, the virus is selected from HIV, Hepatitis A, Hepatitis B, Hepatitis C, Hepatitis D, herpes viruses, papillomaviruses, and influenza.

In a sixth aspect, the present disclosure provides a method of treating septic shock in a subject in need thereof, the method comprising administering to the subject a therapeutically effective amount of a compound of formula (I), or a pharmaceutically acceptable salt thereof.

Unless specifically stated otherwise herein, references made in the singular may also include the plural. For example, "a" and "an" may refer to either one, or one or more.

As used herein, the phase "compound(s) or pharmaceutically acceptable salts thereof" refers to at least one compound, at least one salt of the compounds, or a combination thereof. For example, compounds of formula (I) or pharmaceutically acceptable salts thereof includes a compound of formula (I); two compounds of formula (I); a salt of a compound of formula (I); a compound of formula (I) and one or more salts of the compound of formula (I); and two or more salts of a compound of formula (I).

Unless otherwise indicated, any atom with unsatisfied valences is assumed to have hydrogen atoms sufficient to satisfy the valences.

Throughout the specification, groups and substituents thereof may be chosen by one skilled in the field to provide stable moieties and compounds.

Listed below are definitions of various terms used to describe the present disclosure. These definitions apply to the terms as they are used throughout the specification (unless they are otherwise limited in specific instances) either individually or as part of a larger group. The definitions set forth herein take precedence over definitions set forth in any patent, patent application, and/or patent application publication incorporated herein by reference.

The term "$C_2$-$C_4$alkenyl" as used herein, refers to a hydrocarbon of two to four carbon atoms that contains one or two double bonds.

The term "$C_1$-$C_4$alkoxy" as used herein, refers to a $C_1$-$C_4$alkyl group attached to the parent molecular moiety through an oxygen atom.

The term "$C_1$-$C_4$alkoxycarbonyl" as used herein, refers to a $C_1$-$C_4$alkoxy group attached to the parent molecular moiety through a carbonyl group.

The term "$C_1$-$C_6$alkoxycarbonyl" as used herein, refers to a $C_1$-$C_6$alkoxy group attached to the parent molecular moiety through a carbonyl group.

The term "$C_1$-$C_4$alkoxycarbonylamino" as used herein, refers to a $C_1$-$C_4$alkoxycarbonyl group attached to the parent molecular moiety through an —NH group.

The term "$C_1$-$C_3$alkyl" as used herein, refers to a group derived from a straight or branched chain saturated hydrocarbon containing from one to three carbon atoms.

The term "$C_1$-$C_4$alkyl" as used herein, refers to a group derived from a straight or branched chain saturated hydrocarbon containing from one to four carbon atoms.

The term "$C_1$-$C_6$alkyl" as used herein, refers to a group derived from a straight or branched chain saturated hydrocarbon containing from one to six carbon atoms.

The term "$C_1$-$C_4$alkylcarbonyl" as used herein, refers to a $C_1$-$C_4$alkyl group attached to the parent molecular moiety through a carbonyl group.

The term "$C_1$-$C_3$alkylcarbonylamino" as used herein refers to $R^aC(O)NH$—, wherein $R^a$ is a $C_1$-$C_3$alkyl group.

The term "$C_1$-$C_4$alkylsulfonyl" as used herein, refers to a $C_1$-$C_4$alkyl group attached to the parent molecular moiety through a sulfonyl group.

The term "amido" as used herein, refers to —C(O)NH$_2$.

The term "aminocarbonyl" as used herein, refers to —C(O)NH$_2$.

The term "aminocarbonyl($C_1$-$C_3$alkyl)" as used herein, refers to an aminocarbonyl group attached to the parent molecular moiety through a $C_1$-$C_3$alkyl group.

The term "carbonyl" as used herein, refers to —C(O)—.

The term "carboxy" as used herein, refers to —CO$_2$H.

The term "carboxy$C_2$-$C_6$alkenyl" as used herein, refers to a carboxy group attached to the parent molecular moiety through a $C_2$-$C_6$alkenyl group.

The term "carboxy$C_1$-$C_6$alkyl" as used herein, refers to a carboxy group attached to the parent molecular moiety through a $C_1$-$C_6$alkyl group.

The term "cyano" as used herein, refers to —CN.

The term "$C_3$-$C_6$cycloalkyl" as used herein, refers to a saturated monocyclic hydrocarbon ring system having three to six carbon atoms and zero heteroatoms. Representative examples of cycloalkyl groups include, but are not limited to, cyclopropyl, cyclobutyl, cyclopentyl, and cyclohexyl.

The term "($C_3$-$C_6$cycloalkyl)$C_1$-$C_3$alkyl" as used herein, refers to a $C_1$-$C_3$alkyl group substituted with a $C_3$-$C_6$cycloalkyl group.

The term "formyl" as used herein, refers to —C(O)H.

The terms "halo" and "halogen" as used herein, refer to F, Cl, Br, or I.

The term "halo$C_1$-$C_4$alkoxy" as used herein, refers to a halo$C_1$-$C_4$alkyl group attached to the parent molecular moiety through an oxygen atom.

The term "halo$C_1$-$C_3$alkyl" as used herein, refers to a $C_1$-$C_3$alkyl group substituted with one, two, or three halogen atoms.

The term "halo$C_1$-$C_4$alkyl" as used herein, refers to a $C_1$-$C_4$alkyl group substituted with one, two, or three halogen atoms.

The term "hydroxy$C_1$-$C_3$alkyl" as used herein, refers to a hydroxy group attached to the parent molecular moiety through a $C_1$-$C_3$alkyl group.

The term "hydroxy$C_1$-$C_4$alkyl" as used herein, refers to a hydroxy group attached to the parent molecular moiety through a $C_1$-$C_4$alkyl group.

The term "hydroxy$C_1$-$C_6$alkyl" as used herein, refers to a hydroxy group attached to the parent molecular moiety through a $C_1$-$C_6$alkyl group.

The term "nitro" as used herein, refers to —NO$_2$.

The term "oxo" as used herein, refers to =O.

The term "phenylcarbonyl" as used herein, refers to a phenyl group attached to the parent molecular moiety through a carbonyl group.

The term "phenyloxy" as used herein, refers to a phenyl group attached to the parent molecular moiety through an oxygen atom.

The term "phenyloxycarbonyl" as used herein, refers to a phenyloxy group attached to the parent molecular moiety through a carbonyl group.

The term "pyridinyl($C_1$-$C_3$)alkyl" as used herein, refers to a pyridinyl group attached to the parent molecular moiety through a $C_1$-$C_3$alkyl group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of formula (I) can form salts which are also within the scope of this disclosure. Unless otherwise indicated, reference to an inventive compound is understood to include reference to one or more salts thereof. The term "salt(s)" denotes acidic and/or basic salts formed with inorganic and/or organic acids and bases. In addition, the term "salt(s)" may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the disclosure. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like. Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

Compounds of the present disclosure may contain stereoisomers, wherein asymmetric or chiral centers are present. Specific stereochemistry may be designated by the symbols "R" or "S" depending on the configuration of substituents around the chiral carbon atom. The present invention contemplates various stereoisomers (i.e., enantiomers and diastereomers) and mixtures thereof and is intended to encompass all stereoisomers that bind to PD-L1. Individual stereoisomers of compounds of the present invention may be prepared synthetically from commercially available starting materials which contain asymmetric or chiral centers or by preparation of racemic mixtures followed by resolution well-known to those of ordinary skill in the art.

In addition, compounds of formula (I), subsequent to their preparation, can be isolated and purified to obtain a composition containing an amount by weight equal to or greater than 99% of a compound of formula (I) ("substantially pure"), which is then used or formulated as described herein. Such "substantially pure" compounds of formula (I) are also contemplated herein as part of the present disclosure.

"Stable compound" and "stable structure" are meant to indicate a compound that is sufficiently robust to survive isolation to a useful degree of purity from a reaction mixture, and formulation into an efficacious therapeutic agent. The present disclosure is intended to embody stable compounds.

"Therapeutically effective amount" is intended to include an amount of a compound of the present disclosure alone or an amount of the combination of compounds claimed or an amount of a compound of the present disclosure in combination with other active ingredients effective to inhibit PD-1/PD-L1 protein/protein and/or CD80/PD-L1 protein/protein interactions, or effective to treat or prevent cancer or infectious disease, such as septic shock, HIV or Hepatitis B, Hepatitis C, and Hepatitis D.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present disclosure are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with formula (I) and/or pharmaceutically acceptable salts thereof can be administered by any means suitable for the condition to be treated, which can depend on the need for site-specific treatment or quantity of formula (I) compound to be delivered. Also embraced within this disclosure is a class of pharmaceutical compositions comprising a compound of formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of formula (I) may be administered by any suitable route, preferably in the form of a pharmaceutical composition adapted to such a route, and in a dose effective for the treatment intended. The compounds and compositions of the present disclosure may, for example, be administered orally, mucosally, rectally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, antioxidants, and preserving agents.

A tablet can, for example, be prepared by admixing at least one compound of formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate;

granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of formula (I) and/or at least one salt thereof with at least one inert solid diluent, such as, for example, calcium carbonate; calcium phosphate; and kaolin.

Soft gelatin capsules can, for example, be prepared by mixing at least one compound of formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, antioxidants, e.g., ascorbic acid. In addition, dispersible powders and granules can also contain at least one excipient, including, but not limited to, for example, sweetening agents; flavoring agents; and coloring agents.

An emulsion of at least one compound of formula (I) and/or at least one pharmaceutically acceptable salt thereof can, for example, be prepared as an oil-in-water emulsion. The oily phase of the emulsions comprising compounds of formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceryl distearate alone or with a wax, or other materials well known in the art.

The compounds of formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of formula (I) in an oily phase, such as, for example, a mixture of soybean oil and lecithin; 2) combining the formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this disclosure include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this disclosure can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this disclosure depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this disclosure are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this disclosure comprise at least one compound of formula (I) and/or at least one pharmaceutically acceptable salt thereof, and optionally an additional agent selected from any pharmaceutically acceptable carrier, adjuvant, and vehicle. Alternate compositions of this disclosure comprise a compound of the formula (I) described herein, or a prodrug thereof, and a pharmaceutically acceptable carrier, adjuvant, or vehicle.

The compounds of the disclosure inhibit the PD-1/PD-L1 protein/protein resulting in a PD-L1 blockade. The blockade of PD-L1 can enhance the immune response to cancerous cells and infectious diseases in mammals, including humans.

In one aspect, the present disclosure relates to treatment of a subject in vivo using a compound of formula (I) or a salt thereof such that growth of cancerous tumors is inhibited. A compound of formula (I) or a salt thereof may be used alone to inhibit the growth of cancerous tumors. Alternatively, a compound of formula (I) or a salt thereof may be used in conjunction with other immunogenic agents or standard cancer treatments, as described below.

In one embodiment, the disclosure provides a method of inhibiting growth of tumor cells in a subject, comprising administering to the subject a therapeutically effective amount of a compound of formula (I) or a salt thereof.

In one embodiment, a method is provided for treating cancer comprising administering to a patient in need thereof, a therapeutically effective amount of a compound of formula (I) or a salt thereof. Examples of cancers include those whose growth may be inhibited using compounds of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the compounds of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005) *Int. Immunol.* 17:133-144).

Optionally, the compounds of formula (I) or salts thereof can be combined with another immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173: 4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

In humans, some tumors have been shown to be immunogenic such as melanomas. It is anticipated that by raising the threshold of T cell activation by PD-L1 blockade, tumor responses are expected to be activated in the host.

The PD-L1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogenenic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) *Science* 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (i.e. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV, HDV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269:1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al. (1998) *Cancer Research* 58: 5301-5304). An example of such a combination is a compound of this disclosure in combination with dacarbazine for the treatment of melanoma. Another example of such a combination is a compound of this disclosure in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

The compounds of this disclosure can also be used in combination with bispecific compounds that target Fc alpha or Fc gamma receptor-expressing effectors cells to tumor cells (see, e.g., U.S. Pat. Nos. 5,922,845 and 5,837,243). Bispecific compounds can be used to target two separate antigens. For example anti-Fc receptor/anti tumor antigen (e.g., Her-2/neu) bispecific compounds have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific compounds which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) Science 274: 1363-1365). Inhibitors that bind to and block each of these entities may be used in combination with the compounds of this disclosure to counteract the effects of the immunosuppressive agent and favor tumor immune responses by the host.

Compounds that activate host immune responsiveness can be used in combination with PD-L1 blockade. These include molecules on the surface of dendritic cells which activate DC function and antigen presentation. Anti-CD40 compounds are able to substitute effectively for T cell helper activity (Ridge, J. et al. (1998) *Nature* 393: 474-478) and can be used in conjunction with PD-L1 blockade (Ito, N. et al. (2000) *Immunobiology* 201 (5) 527-40). Activating compounds to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

Other methods of the disclosure are used to treat patients who have been exposed to particular toxins or pathogens. Accordingly, another aspect of the disclosure provides a method of treating an infectious disease in a subject comprising administering to the subject a therapeutically effective amount of a compound of formula (I) or salts thereof.

Similar to its application to tumors as discussed above, the compound of formula (I) or salts thereof can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, C or D), *Influenza, Herpes, Giardia, Malaria, Leishmania, Staphylococcus aureus, Pseudomonas Aeruginosa*. PD-L1 blockade is particularly useful against established infections by agents such as HIV that present altered antigens over the course of the infections. These novel epitopes are recognized as foreign at the time of administration, thus provoking a strong T cell response that is not dampened by negative signals through PD-1.

Some examples of pathogenic viruses causing infections treatable by methods of the disclosure include HIV, hepatitis (A, B, C, or D), herpes viruses (e.g., VZV, HSV-1, HAV-6, HHv-7 HHV-8 HSV-2, CMV, and Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by methods of the disclosure include Candida (albicans, krusei, glabrata, tropicalis, etc.), *Cryptococcus neoformans, Aspergillus (fumigatus, niger, etc.), Genus Mucorales (mucor, absidia, rhizophus), Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

In all of the above methods, PD-L1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123), vaccines, or agents that modify gene expression.

The compounds of this disclosure may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al. (1999) *Proc. Natl. Acad. Sci. U.S.A.* 96: 2982-2987); autoimmune prostatitis evoked by TRAMP tumor cell vaccines (Hurwitz, A. (2000) supra), melanoma peptide antigen vaccination and vitilago observed in human clinical trials (Rosenberg, S A and White, D E (1996) *J. Immunother Emphasis Tumor Immunol* 19 (1): 81-4).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta.peptide in amyloid deposits in the brain; antibody responses against amyloid are able to clear these amyloid deposits (Schenk et al., (1999) Nature 400: 173-177).

Other self proteins may also be used as targets such as IgE for the treatment of allergy and asthma, and TNF.alpha. for rheumatoid arthritis. Finally, antibody responses to various hormones may be induced by the use of a compound of formula (I) or salts thereof. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 antibody can be used for induction of therapeutic autoimmune responses to treat patients having an inappropriate accumulation of other self-antigens, such as amyloid deposits, including A.beta. in Alzheimer's disease, cytokines such as TNF alpha, and IgE.

The compounds of this disclosure may be used to stimulate antigen-specific immune responses by co-administration of a compound of formula (I) or salts thereof with an antigen of interest (e.g., a vaccine). Accordingly, in another aspect the disclosure provides a method of enhancing an immune response to an antigen in a subject, comprising administering to the subject: (i) the antigen; and (ii) a compound of formula (I) or salts thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

As previously described, the compounds of the disclosure can be co-administered with one or more other therapeutic agents, e.g., a cytotoxic agent, a radiotoxic agent or an immunosuppressive agent. The compounds of the disclosure can be administered before, after or concurrently with the other therapeutic agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/mL dose once every 21 days. Co-administration of a compound of formula (I) or salts thereof, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising a compound of formula (I) or salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

The above other therapeutic agents, when employed in combination with the compounds of the present disclosure, may be used, for example, in those amounts indicated in the Physicians' Desk Reference (PDR) or as otherwise determined by one of ordinary skill in the art. In the methods of the present disclosure, such other therapeutic agent(s) may be administered prior to, simultaneously with, or following the administration of the inventive compounds.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

As used in the present specification, the following terms have the meanings indicated: THF for tetrahydrofuran, h or hr for hours, min for minutes, rt or RT or Rt for room temperature or retention time (context will dictate), $t_R$ for retention time, DMSO for dimethylsulfoxide, DMF for N,N-dimethylformamide, and MeOH for methanol.

Intermediate: 4-((4-Bromo-2,3-dihydro-1H-inden-1-yl)oxy)-5-chloro-2-hydroxybenzaldehyde

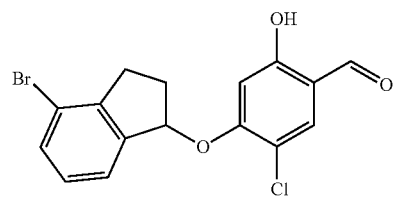 [SMILES: O=Cc1cc(Cl)c(OC2CCc3c(Br)cccc32)cc1O]

Diisopropyl azodicarboxylate (0.76 mL, 3.87 mmol) was added dropwise to a solution of 4-bromo-2,3-dihydro-1H-inden-1-ol (750.0 mg, 3.52 mmol), 5-chloro-2,4-dihydroxybenzaldehyde (607.0 mg, 3.52 mmol) and triphenylphosphine (1.02 g, 3.87 mmol) in dry THF (15 mL) at 0° C. The resultant yellow solution was allowed to warm up to room temperature where it stirred for 16 h. The solvent was removed in vacuo, and the residue was taken up in a small amount of dichloromethane and charged to a RediSepRf normal phase silica gel Teledyne ISCO 80 g disposable column which was first eluted with hexanes for 200 mL, followed by 0-50% B for 1500 mL where solvent B=ethyl acetate and solvent A=hexanes. Fractions containing the desired product were combined and dried via centrifugal evaporation to afford the desired product, 4-((4-bromo-2,3-dihydro-1H-inden-1-yl)oxy)-5-chloro-2-hydroxybenzaldehyde (742.6 mg, 38.9%) as a light yellow solid which was carried forward directly. LCMS: $t_R$ (retention time)=1.50 min. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile: water with 0.05% trifluoroacetic acid; Mobile Phase B=100:0 acetonitrile:water with 0.05% trifluoroacetic acid; Column=Waters Aquity BEH C18, 2.1×50 mm, 1.7 U (=μm); Oven Temp=40° C. $^1$H NMR (500 MHz, DMSO-$d_6$) δ 10.05 (s, 1H), 7.69 (s, 1H), 7.60 (d, J=8.1 Hz, 1H), 7.47 (d, J=7.3 Hz, 1H), 7.26 (t, J=7.7 Hz, 1H), 6.92 (s, 1H), 6.07 (dd, J=6.6, 3.7 Hz, 1H), 3.12-3.01 (m, 1H), 2.98-2.87 (m, 1H), 2.75-2.61 (m, 1H), 2.16-2.07 (m, 1H).

Intermediate: 5-((5-((4-Bromo-2,3-dihydro-1H-inden-1-yl)oxy)-4-chloro-2-formylphenoxy)methyl)-nicotinonitrile

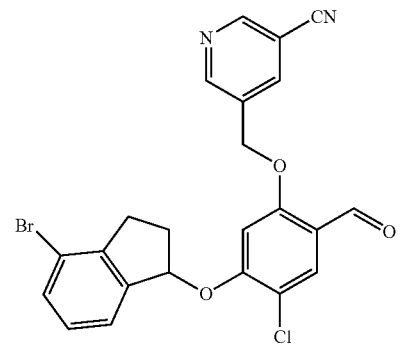 [SMILES: N#Cc1cncc(COc2cc(OC3CCc4c(Br)cccc43)c(Cl)cc2C=O)c1]

A suspension of 4-((4-bromo-2,3-dihydro-1H-inden-1-yl)oxy)-5-chloro-2-hydroxybenzaldehyde (500 mg, 1.36 mmol), 5-(chloromethyl)nicotinonitrile (270 mg, 1.77 mmol) and cesium carbonate (665 mg, 2.04 mmol) in dry DMF (8 mL) was stirred at room temperature for 16 h. The solvent was removed in vacuo, and the residue was partitioned between ethyl acetate and water. The aqueous phase was separated and extracted once more with ethyl acetate. The organic extracts were combined and washed with brine, dried over magnesium sulfate, filtered and concentrated to yield a residue which was triturated with dichloromethane and hexanes to yield the desired product, 5-((5-((4-bromo-2,3-dihydro-1H-inden-1-yl)oxy)-4-chloro-2-formylphenoxy)methyl)nicotino-nitrile (201.2 mg, 28.9%), as a light tan solid after suction-filtration. The filtrate was concentrated and taken up in a small amount of dichloromethane and charged to a RediSepRf normal phase silica gel Teledyne ISCO 40 g disposable column which was first eluted with hexanes for 60 mL, followed by 0-50% B for 600 mL where solvent B=ethyl acetate and solvent A=hexanes. Fractions containing the desired product were combined and dried via centrifugal evaporation to yield additional product (101.3 mg, 10.4%) as a tan solid. Both fractions were later combined and carried forward directly. LCMS: $t_R$=1.43 min; LCMS (ESI) m/z=485.05 [M+H]$^+$. LCMS conditions: Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C. $^1$H NMR (500 MHz, DMSO-$d_6$) δ 10.26 (s, 1H), 9.05 (s, 1H), 9.05 (s, 1H), 8.58-8.55 (m, 1H), 7.73 (s, 1H), 7.61 (d, J=7.7 Hz, 1H), 7.42 (d, J=7.3 Hz, 1H), 7.31-7.13 (m, 2H), 6.31 (dd, J=6.6, 4.0 Hz, 1H), 5.52 (s, 2H), 3.13-3.04 (m, 1H), 2.98-2.88 (m, 1H), 2.76-2.66 (m, 1H), 2.13-2.05 (m, 1H).

Intermediate: 3-((3-Bromo-2-chlorophenoxy)methyl)-1-methylpiperidine

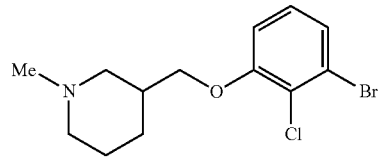 [SMILES: CN1CCCC(COc2cccc(Br)c2Cl)C1]

Potassium carbonate (0.80 g, 5.78 mmol) was added in one portion to a stirred solution of 3-bromo-2-chlorophenol (0.50 g, 2.41 mmol) and 3-(bromomethyl)-1-methylpiperidine hydrobromide (0.66 g, 2.41 mmol) in dry DMF (10 mL). The suspension was stirred at 60° C. for 16 h. After cooling to rt, the mixture was then diluted with ethyl acetate and water. The aqueous phase was separated, and extracted once more with ethyl acetate. The combined organic extract was washed with brine, dried over MgSO$_4$, filtered and concentrated to yield an oil which was taken up in a small amount of dichloromethane and charged to a RediSepRf normal phase silica gel Teledyne ISCO 24 g disposable column which was first eluted with dichloromethane for 100 mL, followed by 0-10% B for 650 mL where solvent B=methanol and solvent A=dichloromethane. After concentration of the eluant, there was isolated the desired product, 3-((3-bromo-2-chlorophenoxy)methyl)-1-methylpiperidine (585.5 mg, 76% yield) as a colorless oil. LCMS: $t_R$=0.97 min; LCMS (ESI) m/z=317.85 and 319.90 [M+H]$^+$. LCMS conditions: Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C. $^1$H NMR (500 MHz, CDCl$_3$) δ 7.21 (dd, J=8.1, 1.0 Hz, 1H), 7.05 (t, J=8.1 Hz, 1H), 6.85 (d, J=8.2 Hz, 1H), 4.06-3.64 (m, 2H), 2.96 (br d, J=10.2 Hz, 1H), 2.74 (br d, J=10.4 Hz, 1H), 2.29 (s, 3H), 2.24-2.14 (m, 1H), 1.99 (br t, J=10.4 Hz, 1H), 1.91 (br t, J=10.2 Hz, 1H), 1.84-1.77 (m, 1H), 1.77-1.69 (m, 1H), 1.69-1.59 (m, 1H), 1.26-1.10 (m, 1H).

Intermediate: 3-((2-chloro-3-(4,4,5,5-tetramethyl-1,3,2-dioxaborolan-2-yl)phenoxy)methyl)-1-methylpiperidine

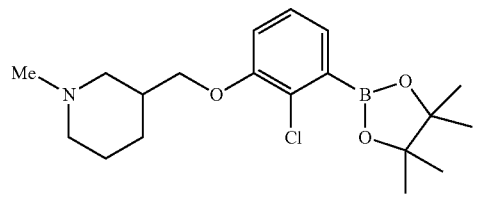 [SMILES: CN1CCCC(COc2cccc(B3OC(C)(C)C(C)(C)O3)c2Cl)C1]

1,1-bis(Diphenylphosphino)ferrocene-palladium(II)dichloride (0.12 g, 0.16 mmol) was added in one portion to an argon-degassed suspension of 3-((3-bromo-2-chlorophenoxy)methyl)-1-methylpiperidine (1.0 g, 3.14 mmol), 4,4,4',4',5,5,5',5'-octamethyl-2,2'-bi(1,3,2-dioxaborolane) (1.20 g, 4.71 mmol), and potassium acetate (0.92 g, 9.42 mmol) in dry dioxane (20 mL) at room temperature in a thick-walled, screw top pressure tube equipped with a magnetic stirrer. The mixture was stirred 95° C. for 4.5 h before it was cooled to room temperature and suction-filtered through Celite to remove the inorganics. The filtrate was then concentrated to yield the crude product as a brown oil which was taken up in a small amount of dichloromethane and charged to a RediSepRf normal phase silica gel Teledyne ISCO 80 g disposable column which was first eluted with dichloromethane for 300 mL, followed by 0-20% B for 1500 mL where solvent A=dichloromethane and solvent B=methanol. Fractions containing the desired product were combined and dried via centrifugal evaporation. There was isolated the desired product (763.1 mg, 66%) as a brown oil which was used as obtained and refrigerated when not in use. LCMS: $t_R$=1.18 min; LCMS (ESI) m/z observed 365.90 [M+H]$^+$ (boronic ester); $t_R$=0.86 min; LCMS (ESI) m/z observed 283.75 [M+H]$^+$ (boronic acid observed in LCMS). LCMS conditions: Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C. $^1$H NMR (500 MHz, CHLOROFORM-d) δ 7.23-7.20 (m, 1H), 7.19-7.14 (m, 1H), 6.95 (dd, J=8.1, 1.5 Hz, 1H), 3.93-3.88 (m, 1H), 3.88-3.82 (m, 1H), 2.99 (br d, J=10.4 Hz, 1H), 2.74 (br d, J=10.7 Hz, 1H), 2.27 (s, 3H), 2.25-2.15 (m, 1H), 2.00-1.92 (m, 1H), 1.91-1.84 (m, 1H), 1.84-1.77 (m, 1H), 1.75-1.69 (m, 1H), 1.68-1.60 (m, 1H), 1.37 (s, 12H), 1.20-1.08 (m, 1H).

25

Intermediate: 5-((4-Chloro-5-((4-(2-chloro-3-((1-methylpiperidin-3-yl)methoxy)phenyl)-2,3-dihydro-1H-inden-1-yl)oxy)-2-formylphenoxy)methyl)nicotinonitrile

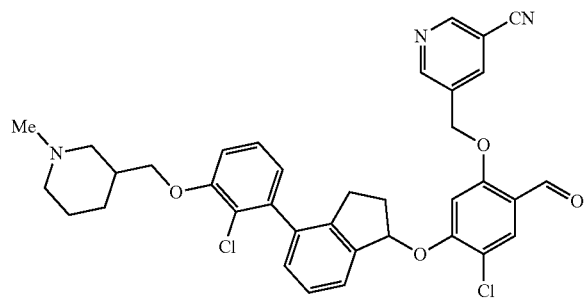 [SMILES: CN1CCCC(COc2cccc(-c3cccc4c3CCC4Oc3cc(OCc4cncc(C#N)c4)c(C=O)cc3Cl)c2Cl)C1]

Second generation XPhos catalyst (16.3 mg, 0.021 mmol) was added to an argon-degassed mixture of 3-((2-chloro-3-(4,4,5,5-tetramethyl-1,3,2-dioxaborolan-2-yl)-phenoxy)methyl)-1-methylpiperidine (126 mg, 0.21 mmol), 5-((5-((4-bromo-2,3-dihydro-1H-inden-1-yl)oxy)-4-chloro-2-formylphenoxy)methyl)nicotinonitrile (100 mg, 0.21 mmol) and potassium phosphate (110 mg, 0.52 mmol) in THF (1.5 mL) and water (0.5 mL) in a 1 dram vial. The vial was sealed and the mixture was stirred at room temperature for 16 h before it was partitioned between ethyl acetate and water. The aqueous phase was separated and extracted once more with ethyl acetate before the organic extracts were combined and washed with brine, dried over MgSO$_4$, filtered and concentrated to yield the crude product as a yellow oil. The crude product was taken up in a small amount of dichloromethane and charged to a RediSepRf normal phase silica gel Teledyne ISCO 24 g disposable column which was first eluted with dichloromethane for 80 mL, followed by 0-20% B for 800 mL where solvent B=methanol and solvent A=dichloromethane. Fractions containing the desired product were combined and dried via centrifugal evaporation to yield the product, 5-((4-chloro-5-((4-(2-chloro-3-((1-methylpiperidin-3-yl)methoxy)phenyl)-2,3-dihydro-1H-inden-1-yl)oxy)-2-formylphenoxy)methyl)nicotinonitrile (124.1 mg, 93%) as a light yellow oil which was refrigerated when not in use. LCMS: $t_R$=1.34 min; LCMS (ESI) m/z=642.10 and 644.05 [M+H]$_+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

26

Example 1001: (2S)-1-(5-Chloro-4-((4-(2-chloro-3-((1-methylpiperidin-3-yl)methoxy)phenyl)-2,3-dihydro-1H-inden-1-yl)oxy)-2-((5-cyanopyridin-3-yl)methoxy)benzyl)piperidine-2-carboxylic acid

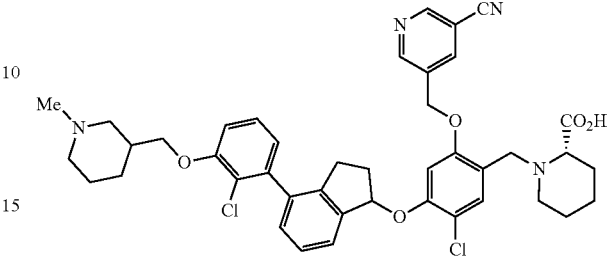

Borane 2-picoline complex (4.1 mg, 0.039 mmol) was added in one portion to a stirred solution of 5-((4-chloro-5-((4-(2-chloro-3-((1-methylpiperidin-3-yl)methoxy)-phenyl)-2,3-dihydro-1H-inden-1-yl)oxy)-2-formylphenoxy)methyl)nicotinonitrile (25.0 mg, 0.039 mmol), (S)-piperidine-2-carboxylic acid (10.1 mg, 0.078 mmol) and acetic acid (50 μL) in dry DMF (0.5 mL) at room temperature. The mixture was stirred for 16 h before the mixture was concentrated to near dryness using nitrogen stream. Afterwards, methanol was added and the resultant suspension was filtered through a syringe and purified via preparative LCMS using the following conditions: Column:)(Bridge C18, 19×200 mm, 5 U; Mobile Phase A: 5:95 acetonitrile: water with 10 mM ammonium acetate; Mobile Phase B: 95:5 acetonitrile: water with 10 mM ammonium acetate; Gradient: 12-52% B over 25 minutes, then a 5 min hold at 100% B; Flow Rate: 20 mL/min; Column Temperature: 25° C. Fraction collection was triggered by MS and UV signals. Fractions containing the desired product were combined and dried via centrifugal evaporation. The yield of the product was 9.7 mg, and its estimated purity by LCMS analysis was 95%. Two analytical LCMS injections were used to determine the final purity. Injection 1 conditions: Column: Waters Acquity UPLC BEH C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 min hold at 100% B; Flow: 1.0 mL/min; Detection: UV at 220 nm. Injection 1 results: Purity: 100.0%; Observed Mass: 755.2; Retention Time: 1.71 min. Injection 2 conditions: Column: Waters Acquity UPLC BEH C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 min hold at 100% B; Flow: 1.0 mL/min; Detection: UV at 220 nm. Injection 1 results: Purity: 94.7%; Observed Mass: 755.2; Retention Time: 1.50 min.

Example 1002: (2R)-2-((5-Chloro-4-((4-(2-chloro-3-((1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid

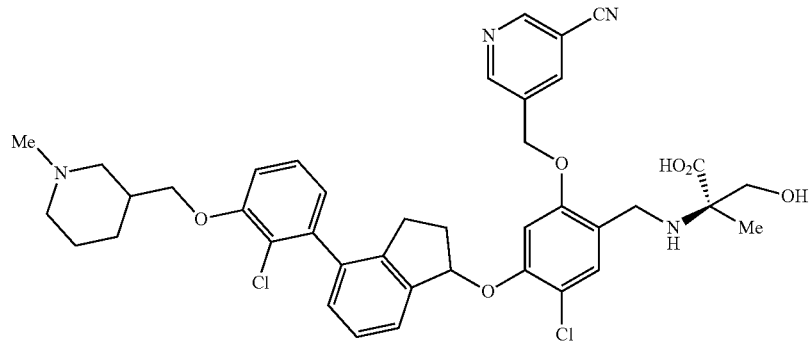 [SMILES: CN1CCCC(COc2cccc(-c3cccc4c3CCC4Oc3cc(OCc4cncc(C#N)c4)c(CN[C@](C)(CO)C(=O)O)cc3Cl)c2Cl)C1]

A solution of 1 M sodium cyanoborohydride in THF (78 μL, 0.078 mmol) was added portionwise after 3 h to a stirred solution of 5-((4-chloro-5-((4-(2-chloro-3-((1-methylpiperidin-3-yl)methoxy)phenyl)-2,3-dihydro-1H-inden-1-yl)oxy)-2-formyl-phenoxy)methyl)nicotinonitrile (25.0 mg, 0.039 mmol), (R)-2-amino-3-hydroxy-2-methylpropanoic acid (9.3 mg, 0.078 mmol), acetic acid (50 μL), 4 Å molecular sieves (25 mg) and two drops of dry triethylamine in dry ethanol (0.5 mL), dichloroethane (0.2 mL), DMF (0.2 mL) and THF (0.2 mL) at room temperature. The mixture was stirred for 16 h before it was concentrated using nitrogen stream. Afterwards, methanol was added and the resultant suspension was filtered through a syringe filter and purified via preparative LCMS using the following conditions: Column: XBridge C18, 19×200 mm, 5 U; Mobile Phase A: 5:95 acetonitrile: water with 10 mM ammonium acetate; Mobile Phase B: 95:5 acetonitrile: water with 10 mM ammonium acetate; Gradient: 10-50% B over 25 minutes, then a 4 min hold at 100% B; Flow Rate: 20 mL/min; Column Temperature: 25° C. Fraction collection was triggered by MS and UV signals. Fractions containing the desired product were combined and dried via centrifugal evaporation. The yield of the product was 5.9 mg, and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 745.15; Retention Time: 1.46 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 99.2%; Observed Mass: 745.15; Retention Time: 1.67 min.

Example 1003: 5-((4-Chloro-5-((4-(2-chloro-3-((1-methylpiperidin-3-yl)methoxy)phenyl)-2,3-dihydro-1H-inden-1-yl)oxy)-2-(hydroxymethyl)phenoxy)-methyl)nicotinonitrile

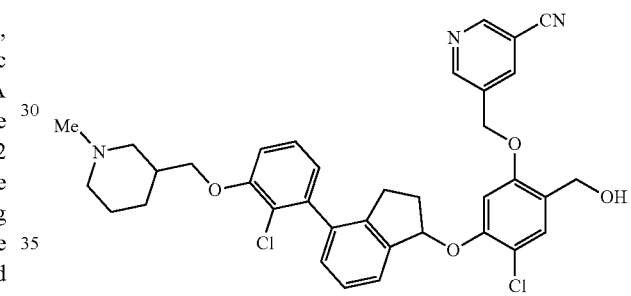

Example 1003 was isolated from the reaction mixture and purification for Example 1002 above. The yield of the product as a triacetic acid salt was 13.7 mg, and its estimated purity by LCMS analysis was 100%. Analytical LCMS was used to determine the final purity. Injection 1 conditions: Column: Waters XBridge C18, 2.1 mm×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1 mL/min; Detection: MS and UV (220 nm). Injection 1 results: Purity: 100.0%; Observed Mass: 644.11; Retention Time: 1.76 min. Injection 2 conditions: Column: Waters XBridge C18, 2.1 mm×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1 mL/min; Detection: MS and UV (220 nm). Injection 2 results: Purity: 100.0%; Observed Mass: 644.11; Retention Time: 2.01 min. $^1$H NMR (500 MHz, METHANOL-$d_4$) δ 8.95 (br s, 1H), 8.90 (br s, 1H), 8.35 (br s, 1H), 7.41 (br s, 1H), 7.37-7.31 (m, 2H), 7.30-7.25 (m, 1H), 7.17 (br d, J=6.7 Hz, 1H), 7.11 (br d, J=7.6 Hz, 1H), 6.99-6.87 (m, 2H), 5.92 (br s, 1H), 5.30 (br s, 2H), 4.64 (br s, 2H), 4.14-4.08 (m, 1H), 4.00 (br t, J=7.3 Hz, 1H), 3.43 (br d, J=8.2 Hz, 1H), 3.38-3.35 (m, 1H), 3.20 (br d, J=9.8 Hz, 1H), 3.05-2.70 (series of m, 3H), 2.63 (br s, 3H), 2.58-2.44 (m, 3H), 2.34 (br s, 1H), 2.16 (br s, 1H), 1.86-1.74 (m, 1H), 1.46-1.35 (m, 1H).

Intermediates: (S)-4-Bromo-2,3-dihydro-1H-inden-1-old and (R)-4-Bromo-2,3-dihydro-1H-inden-1-ol

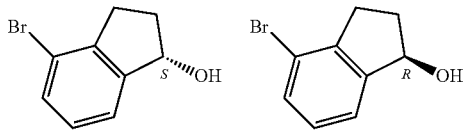

The two enantiomers were obtained from chiral resolution of commercially-available 4-bromo-2,3-dihydro-1H-inden-1-ol (~5.0 g) using the following conditions: Column: ChiralCel OD-H, 30×250 mm, 5 U; Mobile Phase: 10% acetonitrile:ethanol (1:1)/90% $CO_2$; Pressure: 150 bar; Temperature: 30° C.; Flow Rate: 120 mL/min; UV: 220 nm; Injection: 0.25 mL (~160 mg/mL in acetonitrile:ethanol (9:1)) stacked @4.00 min; Fraction Collection: Slope and Level: Peak 1 Window: 4.50-5.80 min, and Peak 2 Window: 5.50-7.50 min. The absolute stereochemistry was determined by X-ray crystallography.

(S)-4-Bromo-2,3-dihydro-1H-inden-1-ol (Peak 1, 2.58 g, off-white solid): LCMS: $t_R$=1.20 min. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (400 MHz, CHLOROFORM-d) δ 7.43 (d, J=8.0 Hz, 1H), 7.36 (d, J=7.5 Hz, 1H), 7.17-7.10 (m, 1H), 5.32 (q, J=5.5 Hz, 1H), 3.08 (ddd, J=16.7, 8.8, 4.6 Hz, 1H), 2.89-2.78 (m, 1H), 2.53 (dddd, J=13.4, 8.5, 7.0, 4.5 Hz, 1H), 2.03-1.91 (m, 1H), 1.84 (br d, J=6.0 Hz, 1H).

(R)-4-Bromo-2,3-dihydro-1H-inden-1-ol (Peak 2, 2.53 g, off-white solid): LCMS: $t_R$=1.205 min. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (400 MHz, CHLOROFORM-d) δ 7.43 (d, J=8.0 Hz, 1H), 7.36 (d, J=7.5 Hz, 1H), 7.17-7.10 (m, 1H), 5.31 (br t, J=6.0 Hz, 1H), 3.08 (ddd, J=16.6, 8.7, 4.5 Hz, 1H), 2.89-2.77 (m, 1H), 2.53 (dddd, J=13.4, 8.5, 7.0, 4.5 Hz, 1H), 2.03-1.91 (m, 1H), 1.85 (br s, 1H).

Example 1004 to Example 1011 were prepared in the same manner as Example 1002 and Example 1003 using chiral materials of 4-bromo-2,3-dihydro-1H-inden-1-ol and 3-((3-bromo-2-chlorophenoxy)methyl)-1-methylpiperidine.

Example 1004: ((R)-2-((5-Chloro-4-(((S)-4-(2-chloro-3-(((R)-1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid

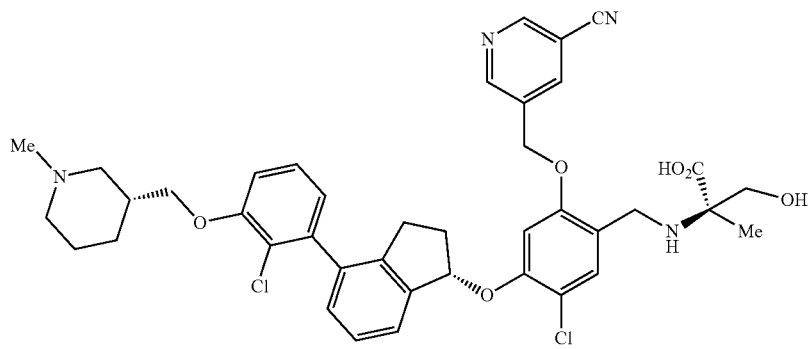 [SMILES: CN1CCC[C@@H](COc2cccc(-c3cccc4c3CC[C@@H]4Oc3cc(OCc4cncc(C#N)c4)c(CN[C@](C)(CO)C(=O)O)cc3Cl)c2Cl)C1]

1 M Sodium cyanotrihydroborate (0.17 mL, 0.17 mmol) was added portionwise after 3 h to a stirred solution of 5-((4-chloro-5-(((S)-4-(2-chloro-3-(((R)-1-methylpiperidin-3-yl)methoxy)phenyl)-2,3-dihydro-1H-inden-1-yl)oxy)-2-formyl-phenoxy)methyl)nicotinonitrile (55.0 mg, 0.086 mmol), (R)-2-amino-3-hydroxy-2-methylpropanoic acid (20.4 mg, 0.17 mmol), acetic acid (0.024 mL, 0.428 mmol), 4 Å powdered molecular sieves (25 mg) and dry triethylamine (two drops) in dry ethanol (0.6 mL), dichloroethane (0.2 mL), DMF (0.1 mL) and THF (0.1 mL) at room temperature. The mixture was stirred for 16 h before it was diluted with DMF and MeOH (1:2) up to 2 mL total volume, filtered through a syringe filter and purified via preparative LCMS with the following conditions: Column XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 22 min, then a 6 min hold at 100% B; Flow Rate: 20 mL/min; Column Temperature: 25° C. Fraction collection was triggered by UV signals. Fractions containing the desired product were combined and dried via centrifugal evaporation. The yield of the product was 39.3 mg (60.9%), and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 99.2%; Observed Mass: 745.15; Retention Time: 1.48 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B;

Flow: 1 mL/min; Detection: MS and UV (220 nm). Injection 2 results: Purity: 98.9%; Observed Mass: 745.16; Retention Time: 1.45 min.

Example 1005: 5-((4-chloro-5-(((S)-4-(2-chloro-3-(((R)-1-methylpiperidin-3-yl)methoxy)phenyl)-2,3-dihydro-1H-inden-1-yl)oxy)-2-(hydroxymethyl)phenoxy)methyl)nicotinonitrile

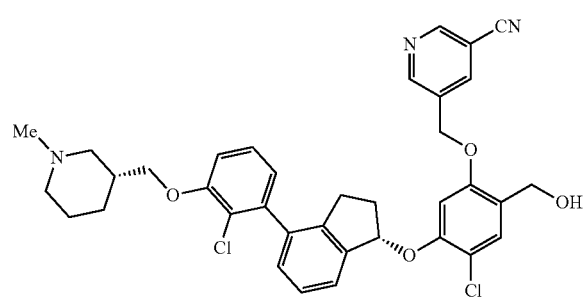 [SMILES: CN1CCC[C@@H](COc2cccc(-c3cccc4c3CC[C@@H]4Oc3cc(OCc4cncc(C#N)c4)c(CO)cc3Cl)c2Cl)C1]

Example 1005 was isolated from the purification of the reaction mixture for Example 1004 above. The yield of the product was 3.6 mg (6.1 mg), and its estimated purity by LCMS analysis was 93%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 94.5%; Observed Mass: 644.08; Retention Time: 1.82 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 93.3%; Observed Mass: 644.08; Retention Time: 1.79 min.

Example 1006: (R)-2-((5-chloro-4-(((R)-4-(2-chloro-3-(((R)-1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 22 min, then a 6 min hold at 100% B; Flow Rate: 20 mL/min; Column Temperature: 25° C. Fraction collection was triggered by UV signals. Fractions containing the desired product were combined and dried via centrifugal evaporation. The yield of the product was 51.9 mg (55.0%), and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 1 results: Purity: 98.4%; Observed Mass: 745.13; Retention Time: 1.6 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 2 results: Purity: 99.5%; Observed Mass: 745.16; Retention Time: 1.54 min.

Example 1007: 5-((4-chloro-5-(((R)-4-(2-chloro-3-(((R)-1-methylpiperidin-3-yl)methoxy)phenyl)-2,3-dihydro-1H-inden-1-yl)oxy)-2-(hydroxymethyl)phenoxy)methyl)nicotinonitrile

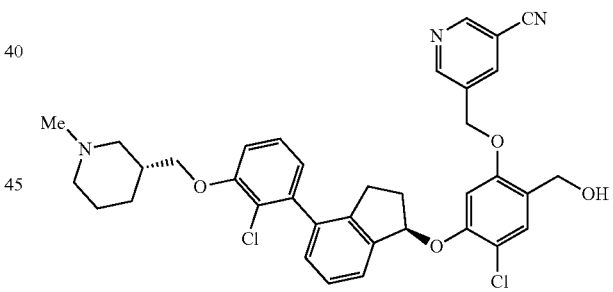

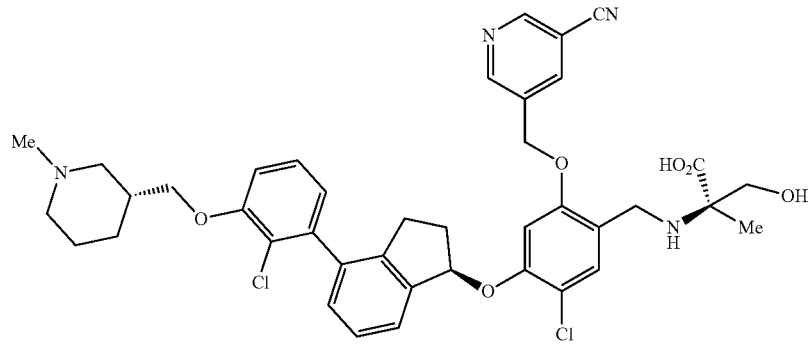 [SMILES: CN1CCC[C@@H](COc2cccc(-c3cccc4c3CC[C@H]4Oc3cc(OCc4cncc(C#N)c4)c(CN[C@](C)(CO)C(=O)O)cc3Cl)c2Cl)C1]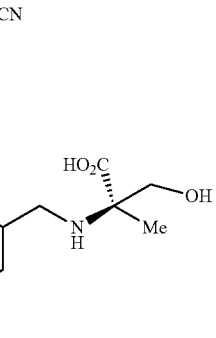

Example 1007 was isolated from the purification of the reaction mixture for Example 1006 above. The yield of the product was 14.5 mg (17.7%), and its estimated purity by LCMS analysis was 98%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 1 results: Purity: 98.2%; Observed Mass: 644.11; Retention Time: 1.76 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 2 results: Purity: 98.7%; Observed Mass: 644.12; Retention Time: 1.9 min.

Example 1008: (R)-2-((5-chloro-4-(((S)-4-(2-chloro-3-(((S)-1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid

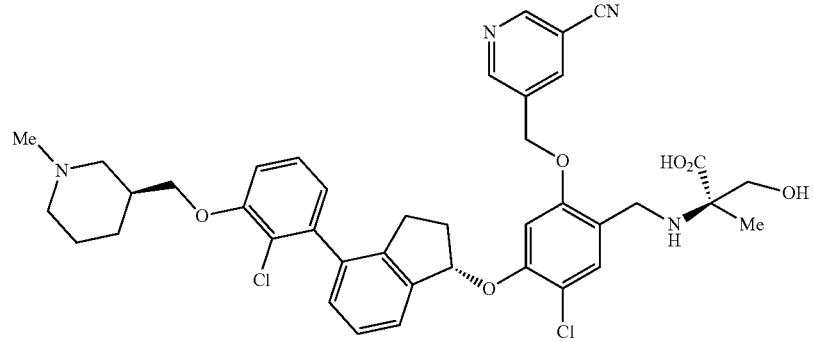 [SMILES: CN1CCC[C@H](COc2cccc(-c3cccc4c3CC[C@@H]4Oc3cc(OCc4cncc(C#N)c4)c(CN[C@](C)(CO)C(=O)O)cc3Cl)c2Cl)C1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 12-52% B over 20 min, then a 5 min hold at 100% B; Flow Rate: 20 mL/min; Column Temperature: 25° C. Fraction collection was triggered by MS and UV signals. Fractions containing the desired product were combined and dried via centrifugal evaporation. The yield of the product was 29.4 mg (56.0%), and its estimated purity by LCMS analysis was 99%. Analytical LCMS was used to determine the final purity. Injection 1 conditions: Column: Waters) XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 100.0%; Observed Mass: 745.13; Retention Time: 1.56 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 99.4%; Observed Mass: 745.14; Retention Time: 1.46 min.

Example 1009: 5-((4-chloro-5-(((S)-4-(2-chloro-3-(((S)-1-methylpiperidin-3-yl)methoxy)phenyl)-2,3-dihydro-1H-inden-1-yl)oxy)-2-(hydroxymethyl)phenoxy)methyl)nicotinonitrile

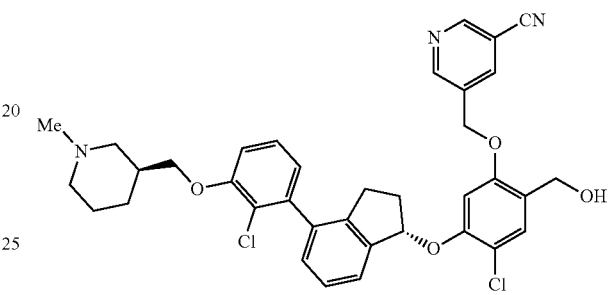

Example 1009 was isolated from the purification of the reaction mixture for Example 1008 above. The yield of the product was 6.5 mg (13.4%), and its estimated purity by LCMS analysis was 93%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 98.1%; Observed Mass: 644.11; Retention Time: 1.92 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 93.3%; Observed Mass: 644.08; Retention Time: 1.77 min.

Example 1010: (R)-2-((5-chloro-4-(((R)-4-(2-chloro-3-(((S)-1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid

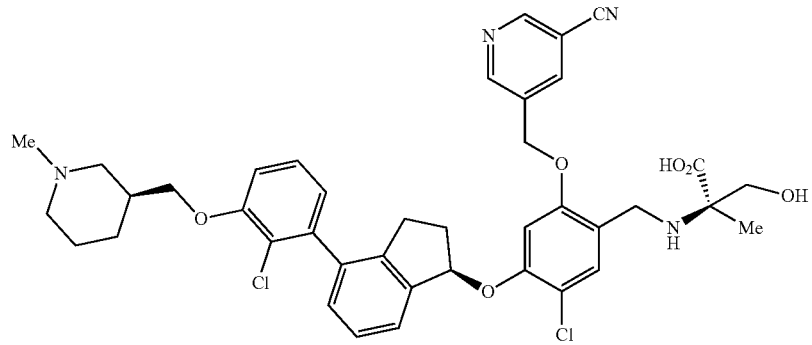 [SMILES: CN1CCC[C@H](COc2cccc(-c3cccc4c3CC[C@H]4Oc3cc(OCc4cncc(C#N)c4)c(CN[C@](C)(CO)C(=O)O)cc3Cl)c2Cl)C1]

The crude material was purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 8-48% B over 25 min, then a 6 min hold at 100% B; Flow Rate: 20 mL/min; Column Temperature: 25° C. Fraction collection was triggered by UV signals. Fractions containing the desired product were combined and dried via centrifugal evaporation. The yield of the product was 46.2 mg (80.0%), and its estimated purity by LCMS analysis was 100%.

Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 100.0%; Observed Mass: 745.17; Retention Time: 1.55 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 100.0%; Observed Mass: 745.13; Retention Time: 1.42 min.

Example 1011: 5-((4-chloro-5-(((R)-4-(2-chloro-3-(((S)-1-methylpiperidin-3-yl)methoxy)phenyl)-2,3-dihydro-1H-inden-1-yl)oxy)-2-(hydroxymethyl)phenoxy)methyl)nicotinonitrile

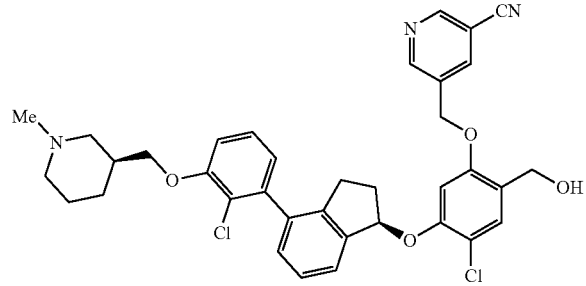 [SMILES: CN1CCC[C@H](COc2cccc(-c3cccc4c3CC[C@H]4Oc3cc(OCc4cncc(C#N)c4)c(CO)cc3Cl)c2Cl)C1]

Example 1011 was isolated from the purification of the reaction mixture for Example 1010 above. The yield of the product was 5.5 mg (10.2%), and its estimated purity by LCMS analysis was 93%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 93.2%; Observed Mass: 644.12; Retention Time: 1.89 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 93.2%; Observed Mass: 644.11; Retention Time: 1.72 min.

Intermediate:
1-Bromo-3-(3-bromopropoxy)-2-chlorobenzene

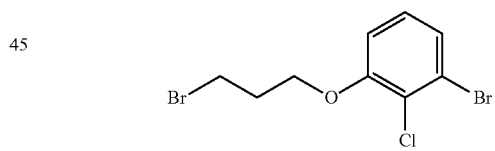

Potassium carbonate (8.3 g, 60.3 mmol) was added in one portion to a stirred solution of 3-bromo-2-chlorophenol (10.0 g, 48.2 mmol) and 1,3-dibromopropane (48.9 mL, 482 mmol) in dry acetone (400 mL). The suspension was stirred at room temperature for 5 d (d=days) before the mixture was suction-filtered to remove the salts. The filtrate was then concentrated in vacuo to a light yellow oil which was transferred to a 250 mL RBF (round bottomed flask) and distilled under high vacuum using a short-path distillation head to remove all of the excess 1,3-dibromopropane which came off between 38-40° C. (bath temp=70° C.) as a colorless liquid. Afterward, there was isolated in the distillation pot the crude desired product as a viscous, honey-colored oil which was considerably pure and thus used 'as is'. It was stored in the refrigerator when not needed.

LCMS: $t_R$=1.46 min. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, CDCl$_3$) δ 7.26 (dd, J=8.0, 1.1 Hz, 1H), 7.09 (t, J=8.2 Hz, 1H), 6.91 (d, J=8.4 Hz, 1H), 4.18 (t, J=5.8 Hz, 2H), 3.67 (t, J=6.3 Hz, 2H), 2.38 (quin, J=6.0 Hz, 2H).

Intermediate:
1-Bromo-3-(3-bromopropoxy)-2-methylbenzene

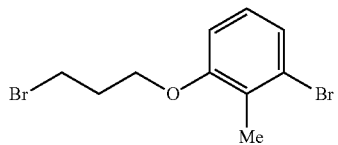 [SMILES: Clc1c(Br)cccc1OCCCBr]

Potassium carbonate (9.2 g, 66.8 mmol) was added in one portion to a stirred solution of 3-bromo-2-methylphenol (10.0 g, 53.5 mmol) and 1,3-dibromopropane (54.3 mL, 535 mmol) in dry acetone (400 mL). The suspension was stirred at room temperature for 6 d before the mixture was suction-filtered to remove the salts. The filtrate was then concentrated in vacuo to a light yellow oil which was transferred to a 250 mL RBF and distilled under high vacuum using a short-path distillation head to remove all of the excess 1,3-dibromopropane which came off between 28-32° C. (bath temp=70° C.) as a colorless liquid. Afterward, there was isolated in the distillation pot the crude desired product as a light yellow-colored oil which was used 'as is' and was stored in the refrigerator when not needed.

LCMS: $t_R$=1.76 min. LCMS conditions: Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, CDCl$_3$) δ 7.18 (d, J=8.0 Hz, 1H), 7.02 (t, J=8.1 Hz, 1H), 6.81 (d, J=8.0 Hz, 1H), 4.11 (t, J=5.8 Hz, 2H), 3.63 (t, J=6.4 Hz, 2H), 2.39-2.34 (m, 2H), 2.33 (s, 3H).

Intermediate: N-(1-(3-(3-Bromo-2-chlorophenoxy)
propyl)piperidin-4-yl)acetamide

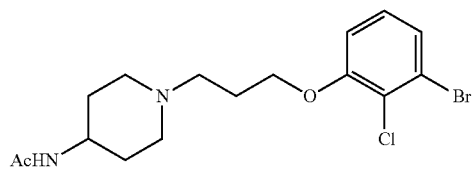 [SMILES: CC(=O)NC1CCN(CCCOc2cccc(Br)c2Cl)CC1]

Potassium carbonate (2.43 g, 17.58 mmol) was added in one portion to a stirred solution of 1-bromo-3-(3-bromopropoxy)-2-chlorobenzene (2.31 g, 7.03 mmol) and N-(piperidin-4-yl)acetamide (1.00 g, 7.03 mmol) in dry acetonitrile (20 mL) and DMF (10 mL). The mixture was heated to 60° C. for 16 h before it was cooled to room temperature and diluted with ethyl acetate and water. The aqueous phase was separated and extracted once more with ethyl acetate. The combined organic phase was washed with brine, dried over magnesium sulfate, filtered and concentrated to ¼ vol. to yield the product, N-(1-(3-(3-bromo-2-chlorophenoxy)-propyl)piperidin-4-yl)acetamide (1.13 g, 41.2%) as a white solid after suction-filtration. The filtrate was concentrated, taken up in a minimal amount of dichloromethane, and charged to a RediSepRf normal phase silica gel Teledyne ISCO 40 g disposable column which was first eluted with dichloromethane for 150 mL, followed by 0-20% B for 1300 mL where solvent A=dichloromethane and solvent B=methanol. Fractions containing the desired product were combined and dried via centrifugal evaporation to yield additional product, N-(1-(3-(3-bromo-2-chlorophenoxy)propyl)-piperidin-4-yl)acetamide (0.62 g, 22.4%) as a white solid.

LCMS: $t_R$=0.86 min; LCMS (ESI) m/z=388.90 and 390.90 [M+H]$^+$. LCMS conditions:

Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, CDCl$_3$) δ 7.23 (dd, J=8.1, 1.2 Hz, 1H), 7.07 (t, J=8.2 Hz, 1H), 6.88 (dd, J=8.2, 0.9 Hz, 1H), 5.38-5.10 (m, 1H), 4.08 (t, J=6.2 Hz, 2H), 3.94-3.64 (m, 1H), 2.86 (br d, J=11.7 Hz, 2H), 2.55 (t, J=7.3 Hz, 2H), 2.13 (br t, J=11.0 Hz, 2H), 2.05-1.99 (m, 2H), 1.98 (s, 3H), 1.94 (br d, J=12.1 Hz, 2H), 1.43 (qd, J=11.6, 3.7 Hz, 2H).

Intermediate: N-(1-(3-(3-Bromo-2-methylphenoxy)
propyl)piperidin-4-yl)acetamide

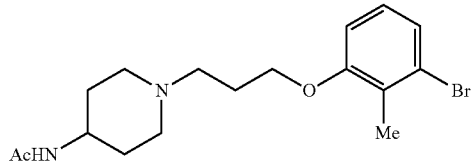 [SMILES: CC(=O)NC1CCN(CCCOc2cccc(Br)c2C)CC1]

Potassium carbonate (607 mg, 4.40 mmol) was added in one portion to a stirred solution of 1-bromo-3-(3-bromopropoxy)-2-methylbenzene (542 mg, 1.76 mmol) and N-(piperidin-4-yl)acetamide (250 mg, 1.76 mmol) in dry DMF (7 mL). The mixture was heated to 60° C. for 16 h before the solvent was removed with a nitrogen stream at room temperature overnight. The residue was taken up in dichloromethane, and the suspension was sonicated for 5 min and suction-filtered to remove the excess potassium carbonate. The filtrate was then concentrated and charged with minimal dichloromethane to a RediSepRf normal phase silica gel Teledyne ISCO 24 g disposable column which was first eluted with dichloromethane for 150 mL, followed by 0-20% B for 600 mL where solvent A=dichloromethane and solvent B=methanol. Fractions containing the desired product were combined and dried via centrifugal evaporation. There was isolated the desired product, N-(1-(3-(3-bromo-2-methylphenoxy)propyl)piperidin-4-yl)acetamide (0.42 g, 64.4%) as a white solid.

LCMS: $t_R$=1.07 min; LCMS (ESI) m/z=368.95 and 370.90 [M+H]$^+$. LCMS conditions: Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, CHLOROFORM-d) δ 7.15 (d, J=8.0 Hz, 1H), 6.99 (t, J=8.1 Hz, 1H), 6.77 (d, J=8.0 Hz, 1H), 5.31 (s, 1H), 4.00 (t, J=6.2 Hz, 2H), 3.90-3.68 (m, 1H), 2.87 (br d, J=11.5 Hz, 2H), 2.53 (t, J=7.4 Hz, 2H), 2.31 (s, 3H), 2.12 (br t, J=10.6 Hz, 2H), 2.01-1.88 (m, 4H), 1.98 (s, 3H), 1.44 (qd, J=11.7, 3.6 Hz, 2H).

Intermediate: (S)-3-((3-(3-Bromo-2-chlorophenoxy)propyl)amino)propane-1,2-diol

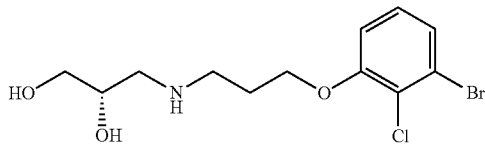 [SMILES: OC[C@@H](O)CNCCCOc1cccc(Br)c1Cl]

Hunig's base (1.6 mL, 9.13 mmol) was added in one portion to a stirred solution of 1-bromo-3-(3-bromopropoxy)-2-chlorobenzene (1.0 g, 3.04 mmol) and (S)-3-amino-propane-1,2-diol (1.4 g, 15.22 mmol) in dry DMF (30 mL). The mixture was then heated to 60° C. for 16 h before it was cooled to room temperature and concentrated with a nitrogen stream. The resultant residue was diluted with methanol (up to 10 mL), filtered through a Whatman 13 mm PVDF syringe filter (45 µM), placed into five pHPLC vials (2 mL) and purified by preparative HPLC in several portions (10-100% B over a 12 min gradient @40 ml/min) using a SunFire C18 column (30×100 mm, 5 U) where Mobile Phase A: 5:95 acetonitrile:water with 10 mM ammonium acetate and Mobile Phase B: 95:5 acetonitrile:water with 10 mM ammonium acetate. Fractions containing the desired product were combined and dried via centrifugal evaporation. There was isolated the purified product, (S)-3-((3-(3-bromo-2-chlorophenoxy)propyl)amino)-propane-1,2-diol (971.0 mg, 94%) as a light yellow viscous oil which solidified to a light yellow solid on standing in the freezer overnight.

LCMS: $t_R$=1.04 min; LCMS (ESI) m/z=338.00 and 340.00 [M+H]$^+$. LCMS conditions: Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, METHANOL-d$_4$) δ 7.30 (dd, J=8.0, 0.9 Hz, 1H), 7.19 (t, J=8.2 Hz, 1H), 7.12-7.05 (m, 1H), 4.21 (t, J=5.7 Hz, 2H), 3.91 (br dd, J=8.7, 3.6 Hz, 1H), 3.63-3.50 (m, 2H), 3.35 (s, 1H), 3.29-3.24 (m, 2H), 3.18 (dd, J=12.5, 3.1 Hz, 1H), 3.02 (dd, J=12.5, 9.3 Hz, 1H), 2.32-2.16 (m, 2H).

Intermediate: (S)-3-((3-(3-Bromo-2-methylphenoxy)propyl)amino)propane-1,2-diol

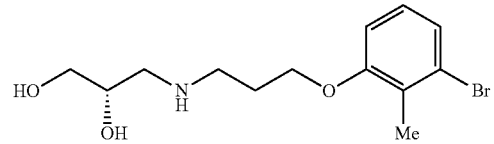 [SMILES: Cc1c(Br)cccc1OCCCNC[C@H](O)CO]

Hunig's base (1.70 mL, 9.74 mmol) was added in one portion to a stirred solution of 1-bromo-3-(3-bromopropoxy)-2-methylbenzene (1.00 g, 3.25 mmol) and (S)-3-aminopropane-1,2-diol (1.48 g, 16.23 mmol) in dry DMF (30 mL). The mixture was then heated to 60° C. for 16 h before it was cooled to room temperature and concentrated with nitrogen stream. The resultant residue was diluted with methanol (up to 10 mL), filtered through a Whatman 13 mm PVDF syringe filter (45 µM), placed into five pHPLC vials (2 mL) and purified by preparative HPLC in several portions (10-100% B over a 12 min gradient @40 ml/min) using a SunFire C18 column (30×100 mm, 5 U) where Mobile Phase A: 5:95 acetonitrile:water with 10 mM ammonium acetate and Mobile Phase B: 95:5 acetonitrile:water with 10 mM ammonium acetate. Fractions containing the desired product were combined and dried via centrifugal evaporation. There was isolated the purified product, (S)-3-((3-(3-bromo-2-methylphenoxy)propyl)amino)-propane-1,2-diol (944.3 mg, 91%) as a colorless oil which solidified to a white solid on standing in the freezer. LCMS: $t_R$=1.07 min; LCMS (ESI) m/z=318.05 and 320.05 [M+H]$^+$. LCMS conditions: Injection Vol=3 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (500 MHz, METHANOL-d$_4$) δ 7.16 (d, J=7.9 Hz, 1H), 7.05 (t, J=8.1 Hz, 1H), 6.92 (d, J=8.2 Hz, 1H), 4.12 (t, J=5.8 Hz, 2H), 3.90 (br dd, J=8.5, 3.6 Hz, 1H), 3.63-3.47 (m, 2H), 3.26-3.19 (m, 2H), 3.16 (dd, J=12.5, 3.1 Hz, 1H), 3.00 (dd, J=12.5, 9.2 Hz, 1H), 2.32 (s, 3H), 2.25-2.14 (m, 2H).

Intermediate: (R)-1-(3-(3-Bromo-2-methylphenoxy)propyl)pyrrolidin-3-ol

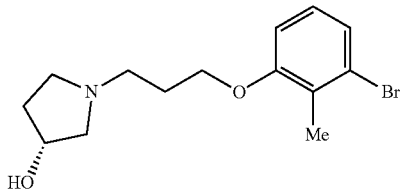 [SMILES: Cc1c(Br)cccc1OCCCN1CC[C@@H](O)C1]

A stirred suspension of 1-bromo-3-(3-chloropropoxy)-2-methylbenzene (5.15 g, 19.54 mmol), (R)-pyrrolidin-3-ol hydrochloride (3.62 g, 29.30 mmol), powdered potassium carbonate (4.05 g, 29.3 mmol) and sodium iodide (2.93 g, 19.54 mmol) in anhydrous DMF (100 mL) was heated at 80° C. for 16 h. The mixture was then cooled to room temperature and the solvent was removed in vacuo. The residue was partitioned between ethyl acetate and water before the aqueous phase was separated and extracted once more with ethyl acetate. The organic extracts were combined, washed with brine, dried over magnesium sulfate, filtered and concentrated to yield a residue which was taken up in a small amount of dichloromethane and charged to a RediSepRf normal phase silica gel Teledyne ISCO 80 g disposable column which was first eluted with dichloromethane for 200 mL, followed by 0-100% B for 1500 mL where solvent A=dichloromethane and solvent B=methanol. Fractions containing the desired product were combined and dried via centrifugal evaporation. There was isolated the product, (R)-1-(3-(3-bromo-2-methylphenoxy)propyl)pyrrolidin-3-ol (5.10 g, 83%) as a caramel-colored oil which was stored in the freezer and used 'as is'. A portion of this product (~33 mg) was purified further for characterization purposes via preparative LCMS with the following conditions: Column:) (Bridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 12-52% B over 20 min, then a 5 min hold at 100% B; Flow: 20 mL/min. Fractions containing the desired product were combined and dried via centrifugal evaporation. The yield of the pure product was 25.1 mg, and its estimated purity by LCMS analysis was 98%. Two analytical LCMS injections were used to determine the final purity. Injection 1 conditions: Column: Waters Acquity UPLC BEH C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75 min hold at 100% B; Flow: 1.0 mL/min; Detection: UV at 220 nm. Injection 1 results: Purity: 98.2%; Observed Mass: 314.0; Retention Time: 1.37 min. Injection 2 conditions: Column: Waters Acquity UPLC BEH C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.75 min hold at 100% B; Flow: 1.0 mL/min; Detection: UV at 220 nm. Injection 2 results: Purity: 98.5%; Observed Mass: 314.0; Retention Time: 1.38 min.

Intermediate: 5-((4-Chloro-2-formyl-5-((4-(4,4,5,5-tetramethyl-1,3,2-dioxaborolan-2-yl)-2,3-dihydro-1H-inden-1-yl)oxy)phenoxy)methyl)nicotinonitrile

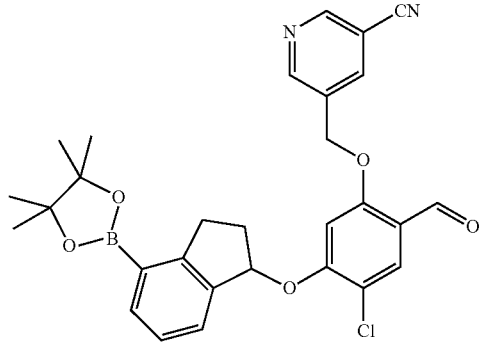 [SMILES: CC1(C)OB(c2cccc3c2CCC3Oc2cc(OCc3cncc(C#N)c3)c(C=O)cc2Cl)OC1(C)C]

1,1-bis(Diphenylphosphino)ferrocene-palladium(II)dichloride (193 mg, 2.64 μmol) was added in one portion to an argon-degassed suspension of 5-((5-((4-bromo-2,3-dihydro-1H-inden-1-yl)oxy)-4-chloro-2-formylphenoxy)methyl)nicotinonitrile (1.70 g, 3.51 mmol), 4,4,4',4',5,5,5',5'-octamethyl-2,2'-bi(1,3,2-dioxaborolane) (0.98 g, 3.87 mmol), and potassium acetate (1.04 g, 10.54 mmol) in dry dioxane (35 mL) at room temperature in a thick-walled pressure tube. The mixture was stirred and heated at 80° C. for 10 h before it was cooled to room temperature, and diluted with ethyl acetate and water. (a pilot scale reaction (50 mg) was done prior to this reaction and its mixture was added to this one prior to extractive workup.) The aqueous phase was separated and extracted once more with ethyl acetate and the combined organic extract was washed with brine, dried over magnesium sulfate, filtered and concentrated to yield the crude product as a dark brown oil. The crude product was then taken up in a small amount of dichloromethane and charged to a RediSepRf normal phase silica gel Teledyne ISCO 80 g disposable column which was first eluted with dichloromethane for 300 mL, followed by 0-40% B for 2700 mL where solvent A=hexanes and solvent B=ethyl acetate. Fractions containing the desired product were combined and dried via centrifugal evaporation. There was isolated the 5-((4-chloro-2-formyl-5-((4-(4,4,5,5-tetramethyl-1,3,2-dioxaborolan-2-yl)-2,3-dihydro-1H-inden-1-yl)oxy)phenoxy)methyl)-nicotinonitrile (1.36 g, 72.7%) as an off-white solid which was carried forward directly and used 'as is'.

LCMS: $t_R$=1.72 min; LCMS (ESI) m/z=531.10 [M+H]$^+$. LCMS conditions: Injection Vol=1 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

$^1$H NMR (400 MHz, DMSO-$d_6$) δ 10.25 (s, 1H), 9.05 (s, 1H), 9.05 (s, 1H), 8.57 (t, J=2.0 Hz, 1H), 7.71 (s, 1H), 7.68 (dd, J=7.3, 1.0 Hz, 1H), 7.52 (d, J=7.3 Hz, 1H), 7.27 (s, 1H), 7.25 (s, 1H), 6.20 (br d, J=3.0 Hz, 1H), 5.53 (s, 2H), 3.27-3.16 (m, 1H), 3.13-3.03 (m, 1H), 2.64-2.53 (m, 1H), 2.06-1.99 (m, 1H), 1.31 (s, 12H).

Intermediate: 5-((4-Chloro-2-formyl-5-((4-(3-(3-((R)-3-hydroxypyrrolidin-1-yl)propoxy)-2-methylphenyl)-2,3-dihydro-1H-inden-1-yl)oxy)phenoxy)methyl)nicotinonitrile

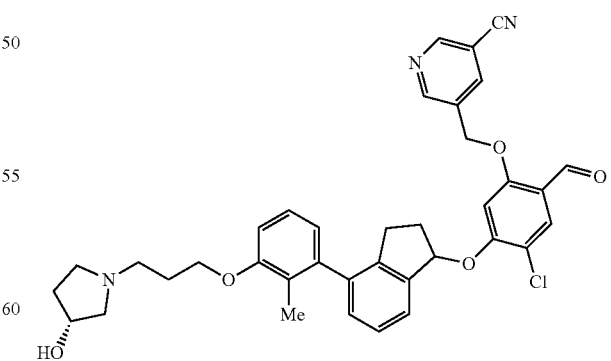

Second generation XPhos precatalyst (34 mg, 0.043 mmol) was added in one portion to an argon-degassed mixture of (R)-1-(3-(3-bromo-2-methylphenoxy)propyl)pyrrolidin-3-ol (134 mg, 0.43 mmol), 5-((4-chloro-2- formyl-5-((4-(4,4,5,5-tetramethyl-1,3,2-dioxaborolan-2-yl)-2,3-dihydro-1H-inden-1-yl)oxy)phenoxy)methyl)-nicotinonitrile (250 mg, 0.47 mmol) and potassium phosphate (227 mg, 1.07 mmol) in THF (4 mL) and water (1 mL) at room temperature. The vial was sealed and the resultant suspension was stirred for 16 h before it was diluted with ethyl acetate and water. The aqueous layer was separated, and extracted once more with ethyl acetate. The combined organic extract was then washed with brine, dried over magnesium sulfate, filtered and concentrated. The crude product was taken up in a small amount of dichloromethane and charged to a RediSepRf normal phase silica gel Teledyne ISCO 25 g disposable column which was first eluted with dichloromethane for 60 mL, followed by 0-10% B for 600 mL where solvent A=dichloromethane and solvent B=methanol. Fractions containing the desired product were combined and dried via centrifugal evaporation. There was isolated the desired product, 5-((4-chloro-2-formyl-5-((4-(3-(3-((R)-3-hydroxypyrrolidin-1-yl)propoxy)-2-methylphenyl)-2,3-dihydro-1H-inden-1-yl)oxy)phenoxy)methyl)-nicotinonitrile (171.4 mg, 62.7%) as a straw-colored oil and additional product, 5-((4-chloro-2-formyl-5-((4-(3-(3-((R)-3-hydroxypyrrolidin-1-yl)propoxy)-2-methylphenyl)-2,3-dihydro-1H-inden-1-yl)oxy)phenoxy)methyl)nicotinonitrile (25.2 mg, 9.2%) as a light orange solid taken as the center cut for characterization purposes.

LCMS: $t_R$=1.86 min; LCMS (ESI) m/z=638.50 [M+H]$^+$. LCMS conditions: Injection Vol=1 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

Example 1012: (2R)-2-((5-Chloro-2-((5-cyanopyridin-3-yl)methoxy)-4-((4-(3-(3-((R)-3-hydroxypyrrolidin-1-yl)propoxy)-2-methylphenyl)-2,3-dihydro-1H-inden-1-yl)oxy)benzyl)-amino)-3-hydroxy-2-methylpropanoic acid 1 M Sodium cyanotrihydroborate (0.10 mL, 0.094 mmol) was added portionwise after 3 h to a stirred solution of 5-((4-chloro-2-formyl-5-((4-(3-(3-((R)-3-hydroxy-pyrrolidin-1-yl)propoxy)-2-methylphenyl)-2,3-dihydro-1H-inden-1-yl)oxy)phenoxy)-methyl)nicotinonitrile (30.0 mg, 0.047 mmol), (R)-2-amino-3-hydroxy-2-methylpropanoic acid (11.2 mg, 0.094 mmol), acetic acid (13 µL, 0.235 mmol), and 4A powdered molecular sieves (25 mg) in dry DMF (0.50 mL) and MeOH (0.42 mL) at room temperature. The mixture was stirred at room temperature for 16 h before it was diluted with DMF and MeOH (1:2) up to 2 mL total volume, filtered through a syringe filter and purified via preparative LCMS with the following conditions: Column XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 11-51% B over 20 min, then a 4 min hold at 100% B; Flow Rate: 20 mL/min; Column Temperature: 25° C. Fraction collection was triggered by UV signals. Fractions containing the desired product were combined and dried via centrifugal evaporation. The yield of the product was 17.7 mg (50.3%), and its estimated purity by LCMS analysis was 99%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 100.0%; Observed Mass: 741.19; Retention Time: 1.51 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 99.1%; Observed Mass: 741.19; Retention Time: 1.5 min.

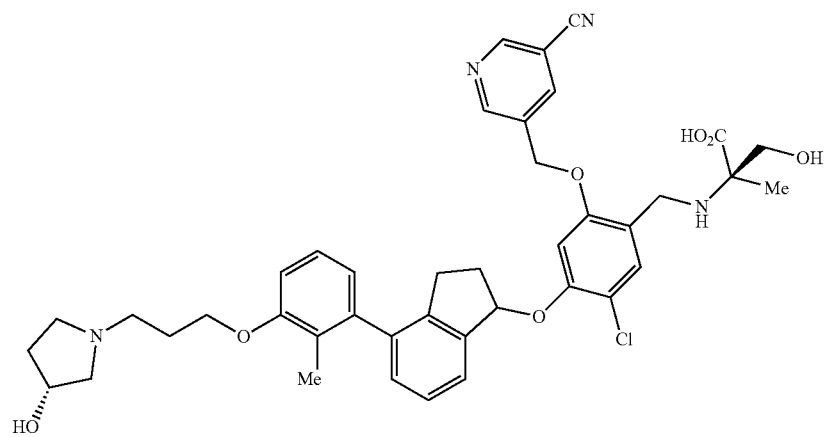 [SMILES: Cc1c(OCCCN2CC[C@@H](O)C2)cccc1-c1cccc2c1CCC2Oc1cc(OCc2cncc(C#N)c2)c(CN[C@](C)(CO)C(=O)O)cc1Cl]

Example 1013: 5-((4-Chloro-2-(hydroxymethyl)-5-((4-(3-(3-((R)-3-hydroxypyrrolidin-1-yl)propoxy)-2-methylphenyl)-2,3-dihydro-1H-inden-1-yl)oxy)phenoxy)methyl)nicotinonitrile

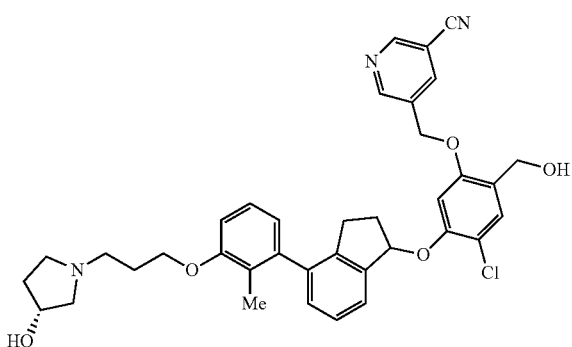 [SMILES: Cc1c(OCCCN2CC[C@@H](O)C2)cccc1-c1cccc2c1CCC2Oc1cc(OCc2cncc(C#N)c2)c(CO)cc1Cl]

Example 1013 was isolated from the purification of the reaction mixture for Example 1012 above. The yield of the product was 10.7 mg (33.3%), and its estimated purity by LCMS analysis was 94%. Analytical LCMS was used to determine the final purity. Injection 1 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 1 results: Purity: 93.6%; Observed Mass: 640.24; Retention Time: 1.81 min. Injection 2 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 2 results: Purity: 95.1%; Observed Mass: 640.25; Retention Time: 1.92 min.

Example 1014: (2S)-1-(5-Chloro-2-((5-cyanopyridin-3-yl)methoxy)-4-((4-(3-(3-((R)-3-hydroxypyrrolidin-1-yl)propoxy)-2-methylphenyl)-2,3-dihydro-1H-inden-1-yl)oxy)benzyl)-piperidine-2-carboxylic acid 1 M Sodium cyanotrihydroborate (0.10 mL, 0.094 mmol) was added portionwise after 3 h to a stirred solution of 5-((4-chloro-2-formyl-5-((4-(3-(3-((R)-3-hydroxy-pyrrolidin-1-yl)propoxy)-2-methylphenyl)-2,3-dihydro-1H-inden-1-yl)oxy)phenoxy)-methyl)nicotinonitrile (30.0 mg, 0.047 mmol), (S)-piperidine-2-carboxylic acid (12.1 mg, 0.094 mmol), acetic acid (13 μL, 0.235 mmol), and 4 Å powdered molecular sieves (25 mg) in dry DMF (0.50 mL) and MeOH (0.42 mL) at room temperature. The mixture was stirred at room temperature for 16 h before it was diluted with DMF and MeOH (1:2) up to 2 mL total volume, filtered through a syringe filter and purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 10-50% B over 25 min, then a 5 min hold at 100% B; Flow Rate: 20 mL/min; Column Temperature: 25° C. Fraction collection was triggered by MS and UV signals. Fractions containing the desired product were combined and dried via centrifugal evaporation. The yield of the product was 25.6 mg (67.5%), and its estimated purity by LCMS analysis was 93%. Analytical LCMS was used to determine the final purity.

Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 95.7%; Observed Mass: 751.23; Retention Time: 1.61 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 93.1%; Observed Mass: 751.21; Retention Time: 1.52 min.

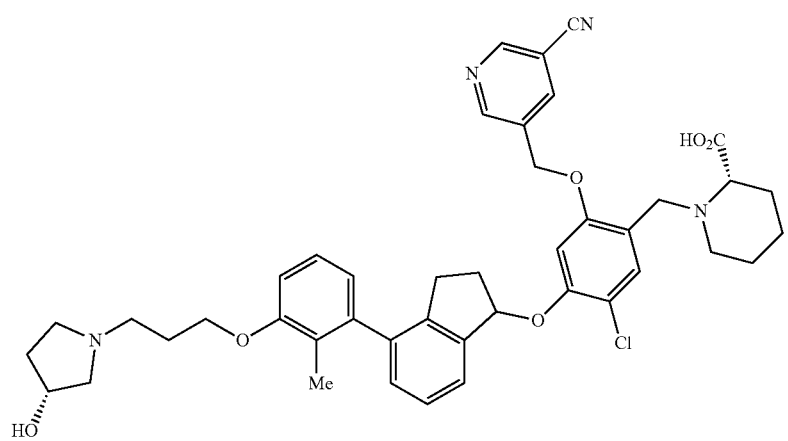 [SMILES: Cc1c(OCCCN2CC[C@@H](O)C2)cccc1-c1cccc2c1CCC2Oc1cc(OCc2cncc(C#N)c2)c(CN2CCCC[C@H]2C(=O)O)cc1Cl]

Example 1015: (5-chloro-2-((5-cyanopyridin-3-yl)methoxy)-4-((4-(3-(3-((R)-3-hydroxypyrrolidin-1-yl)propoxy)-2-methylphenyl)-2,3-dihydro-1H-inden-1-yl)oxy)benzyl)-L-homoserine

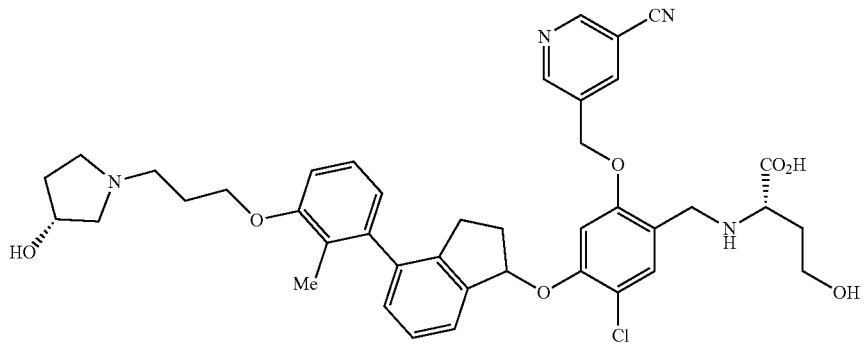 [SMILES: Cc1c(OCCCN2CC[C@@H](O)C2)cccc1-c1cccc2c1CCC2Oc1cc(OCc2cncc(C#N)c2)c(CN[C@@H](CCO)C(=O)O)cc1Cl]

1 M Sodium cyanotrihydroborate (0.10 mL, 0.094 mmol) was added portionwise after 3 h to a stirred solution of 5-((4-chloro-2-formyl-5-((4-(3-(3-((R)-3-hydroxy-pyrrolidin-1-yl)propoxy)-2-methylphenyl)-2,3-dihydro-1H-inden-1-yl)oxy)phenoxy)-methyl)nicotinonitrile (30.0 mg, 0.047 mmol), L-homoserine (11.2 mg, 0.094 mmol), acetic acid (13 µL, 0.24 mmol), and 4A powdered molecular sieves (25 mg) in dry DMF (0.50 mL) and MeOH (0.42 mL) at room temperature. The mixture was stirred at room temperature for 16 h before it was diluted with DMF and MeOH (1:2) up to 2 mL total volume, filtered through a syringe filter and purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 9-49% B over 20 min, then a 5 min hold at 100% B; Flow Rate: 20 mL/min; Column Temperature: 25° C. Fraction collection was triggered by MS and UV signals. Fractions containing the desired product were combined and dried via centrifugal evaporation. The yield of the product was 25.9 mg (71.8%), and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 98.7%; Observed Mass: 741.19; Retention Time: 1.55 min. Injection 2 conditions: Column: Waters XBridge C18, 2.1×50 mm, 1.7 U; Mobile Phase A: 5:95 methanol:water with 10 mM ammonium acetate; Mobile Phase B: 95:5 methanol:water with 10 mM ammonium acetate; Temperature: 50° C.; Gradient: 0-100% B over 3.5 min, then a 0.5 min hold at 100% B; Flow: 0.5 mL/min; Detection: MS and UV (220 nm). Injection 2 results: Purity: 96.6%; Observed Mass: 741.19; Retention Time: 2.87 min.

Intermediate: N-(1-(3-(2-Chloro-3-(1-(2-chloro-5-((5-cyanopyridin-3-yl)methoxy)-4-formylphenoxy)-2,3-dihydro-1H-inden-4-yl)phenoxy)propyl)piperidin-4-yl)acetamide

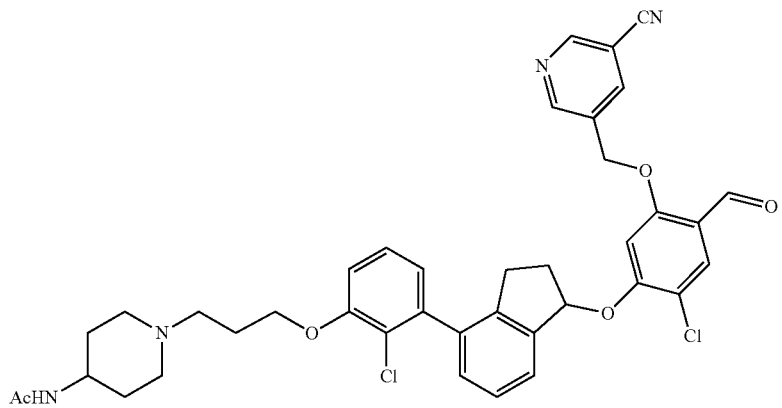 [SMILES: CC(=O)NC1CCN(CCCOc2cccc(-c3cccc4c3CCC4Oc3cc(OCc4cncc(C#N)c4)c(C=O)cc3Cl)c2Cl)CC1]

Second generation Xphos precatalyst (34 mg, 0.043 mmol) was added in one portion to an argon-degassed mixture of N-(1-(3-(3-bromo-2-chlorophenoxy)propyl)-piperidin-4-yl)acetamide (167 mg, 0.43 mmol), 5-((4-chloro-2-formyl-5-((4-(4,4,5,5-tetramethyl-1,3,2-dioxaborolan-2-yl)-2,3-dihydro-1H-inden-1-yl)oxy)phenoxy)methyl)-nicotinonitrile (250 mg, 0.47 mmol) and potassium phosphate (227 mg, 1.07 mmol) in THF (4 mL) and water (1 mL) at room temperature. The vial was then sealed and the resultant suspension was stirred for 16 h before it was diluted with ethyl acetate and water. The aqueous layer was separated, and extracted once more with ethyl acetate before the combined organic extract was washed with brine, dried over magnesium sulfate, filtered and concentrated to yield an brown oil which was diluted with DMF, THF and methanol (2:1:1 mL), filtered through a Whatman Puradisc 13 mm PVDF syringe filter (45 μM), placed into two pHPLC vials (2 mL) and purified by preparative HPLC in four portions (10-100% B over a 10 min gradient @40 ml/min) using a Waters XBridge C18 OBD column (30×100 mm, 5 U) where Mobile Phase A was 10:90 acetonitrile:water with 0.1% trifluoroacetic acid and Mobile Phase B was 90:10 acetonitrile:water with 0.1% trifluoroacetic acid. UV wavelength of 220 nm. Fractions containing the desired product were combined and dried via centrifugal evaporation to yield the product, N-(1-(3-(2-chloro-3-(1-(2-chloro-5-((5-cyanopyridin-3-yl)methoxy)-4-formylphenoxy)-2,3-dihydro-1H-inden-4-yl)phenoxy)propyl)piperidin-4-yl)acetamide (186.5 mg, 61.0%) as a colorless oil.

LCMS: $t_R$=1.29 min; LCMS (ESI) m/z=713.15 and 715.10 [M+H]$^+$. LCMS conditions: Injection Vol=3 μL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

Example 1016: (2R)-2-((4-((4-(3-(3-(4-Acetamidopiperidin-1-yl)propoxy)-2-chlorophenyl)-2,3-dihydro-1H-inden-1-yl)oxy)-5-chloro-2-((5-cyanopyridin-3-yl)methoxy)benzyl)amino)-3-hydroxy-2-methylpropanoic acid 1H-inden-4-yl)phenoxy)propyl)piperidin-4-yl)acetamide (25.0 mg, 0.035 mmol), acetic acid (10 μl, 0.175 mmol), 4 Å molecular sieves (25 mg) and dry TEA (two drops) in dry DMF (0.3 mL), methanol (0.2 mL), ethanol (0.1 mL) and THF (0.1 mL) at room temperature. The mixture was stirred at rt for 16 h before it was filtered through a syringe filter and diluted with DMF and MeOH (1:2) up to 2 mL total volume and purified via preparative LCMS with the following conditions: Column:)(Bridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 6-46% B over 20 min, then a 5-minute hold at 100% B; Flow Rate: 25 mL/min; Column Temperature: 25° C. Fraction collection was triggered by UV signals. Fractions containing the desired product were combined and dried via centrifugal evaporation. The yield of the product was 3.7 mg (12.3%), and its estimated purity by LCMS analysis was 95%.

Analytical LCMS was used to determine the final purity. Injection 1 conditions: Column: Waters XBridge C18, 2.1× 50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 95.4%; Observed Mass: 816.17; Retention Time: 1.78 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1%

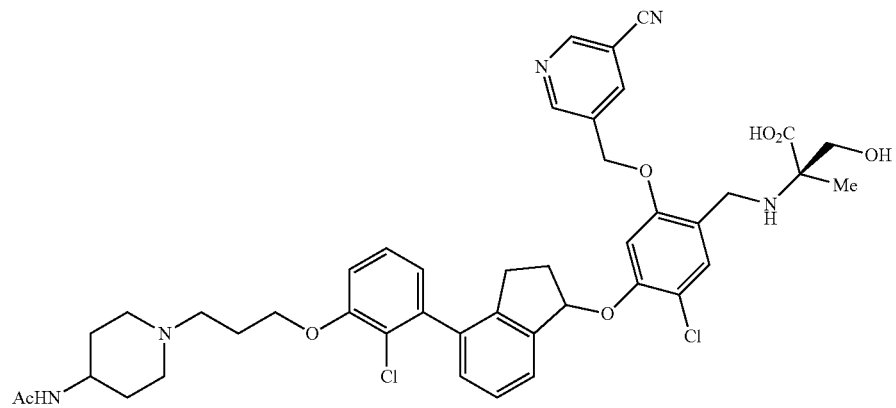 [SMILES: CC(=O)NC1CCN(CCCOc2cccc(-c3cccc4c3CCC4Oc3cc(OCc4cncc(C#N)c4)c(CN[C@](C)(CO)C(=O)O)cc3Cl)c2Cl)CC1]

1 M Sodium cyanotrihydroborate (70 μL, 0.070 mmol) was added portionwise after 3 h to a stirred solution of (R)-2-amino-3-hydroxy-2-methylpropanoic acid (8.4 mg, 0.070 mmol), N-(1-(3-(2-chloro-3-(1-(2-chloro-5-((5-cyanopyridin-3-yl)methoxy)-4-formylphenoxy)-2,3-dihydrotrifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 99.0%; Observed Mass: 816.18; Retention Time: 1.49 min.

Example 1017: (2S)-1-(4-((4-(3-(3-(4-Acetamidopi-
peridin-1-yl)propoxy)-2-chlorophenyl)-2,3-dihydro-
1H-inden-1-yl)oxy)-5-chloro-2-((5-cyanopyridin-3-
yl)methoxy)benzyl)piperidine-2-carboxylic acid

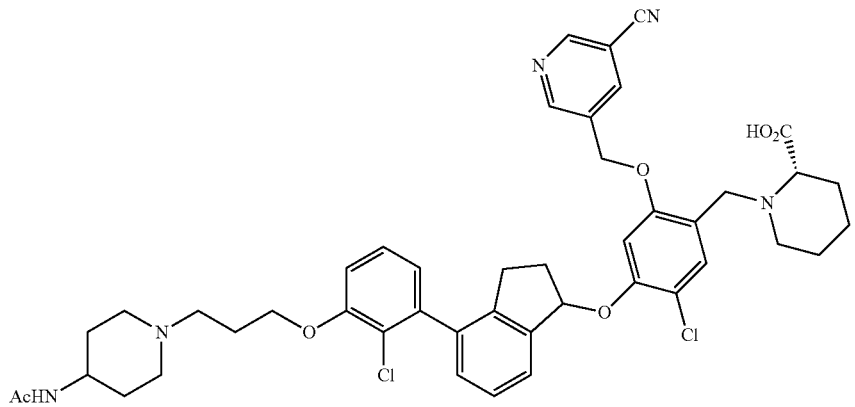 [SMILES: CC(=O)NC1CCN(CCCOc2cccc(-c3cccc4c3CCC4Oc3cc(OCc4cncc(C#N)c4)c(CN4CCCC[C@H]4C(=O)O)cc3Cl)c2Cl)CC1]

1 M Sodium cyanotrihydroborate (70 µL, 0.070 mmol) was added portionwise after 3 h to a stirred solution of N-(1-(3-(2-chloro-3-(1-(2-chloro-5-((5-cyanopyridin-3-yl)methoxy)-4-formylphenoxy)-2,3-dihydro-1H-inden-4-yl)phenoxy)propyl)piperidin-4-yl)acetamide (25.0 mg, 0.035 mmol), (S)-piperidine-2-carboxylic acid (9.1 mg, 0.070 mmol), acetic acid (10 µl, 0.175 mmol), 4 Å powdered molecular sieves (25 mg) and dry TEA (two drops) in dry DMF (0.75 mL) and THF (0.5 mL) at room temperature. The mixture was stirred for 16 h before it was diluted with DMF and MeOH (1:2) up to 2 mL total volume, filtered through a syringe filter and purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 8-48% B over 20 min, then a 5 min hold at 100% B; Flow Rate: 25 mL/min; Column Temperature: 25° C. Fraction collection was triggered by UV signals. Fractions containing the desired product were combined and dried via centrifugal evaporation. The yield of the product was 5.2 mg (16.4%), and its estimated purity by LCMS analysis was 91%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 100.0%; Observed Mass: 826.19; Retention Time: 1.59 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 91.1%; Observed Mass: 826.19; Retention Time: 1.53 min.

Example 1018: (4-((4-(3-(3-(4-Acetamidopiperidin-
1-yl)propoxy)-2-chlorophenyl)-2,3-dihydro-1H-in-
den-1-yl)oxy)-5-chloro-2-((5-cyanopyridin-3-yl)
methoxy)benzyl)-L-homoserine

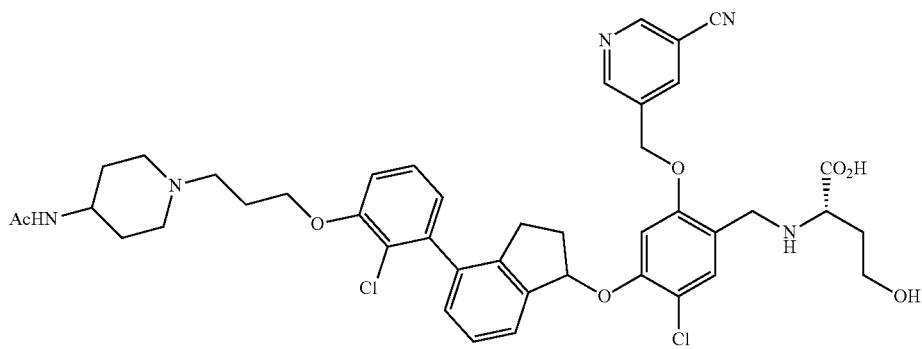 [SMILES: CC(=O)NC1CCN(CCCOc2cccc(-c3cccc4c3CCC4Oc3cc(OCc4cncc(C#N)c4)c(CN[C@@H](CCO)C(=O)O)cc3Cl)c2Cl)CC1]

1 M Sodium cyanotrihydroborate (80 µL, 0.080 mmol) was added portionwise after 3 h to a stirred solution of L-homoserine (9.7 mg, 0.081 mmol), N-(1-(3-(2-chloro-3-(1-(2-chloro-5-((5-cyanopyridin-3-yl)methoxy)-4-formylphenoxy)-2,3-dihydro-1H-inden-4-yl)phenoxy)propyl)piperidin-4-yl)acetamide (29.0 mg, 0.041 mmol), acetic acid (12 µL, 0.20 mmol), 4 Å powdered molecular sieves (25 mg) and dry TEA (two drops) in dry DMF (0.1 mL), ethanol (0.2 mL), dichloroethane (0.1 mL) and THF (0.1 mL) at room temperature. The mixture was stirred at room temperature for 16 h before it was diluted with DMF and MeOH (1:2) up to 2 mL total volume, filtered through a syringe filter and purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 7-47% B over 25 min, then a 5 min hold at 100% B; Flow Rate: 20 mL/min; Column Temperature: 25° C. Fraction collection was triggered by MS and UV signals. Fractions containing the desired product were combined and dried via centrifugal evaporation. The yield of the product was 1.8 mg (5.3%), and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile: water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 98.4%; Observed Mass: 816.2; Retention Time: 1.52 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 97.2%; Observed Mass: 816.15; Retention Time: 1.38 min.

Intermediate: 5-((4-Chloro-5-((4-(2-chloro-3-(3-(((S)-2,3-dihydroxypropyl)amino)propoxy)phenyl)-2,3-dihydro-1H-inden-1-yl)oxy)-2-formylphenoxy) methyl)nicotinonitrile Second generation XPhos precatalyst (30 mg, 0.038 mmol) was added in one portion to an argon-degassed mixture of (S)-3-((3-(3-bromo-2-chlorophenoxy)-propyl) amino)propane-1,2-diol (128 mg, 0.38 mmol), 5-((4-chloro-2-formyl-5-((4-(4,4,5,5-tetramethyl-1,3,2-dioxaborolan-2-yl)-2,3-dihydro-1H-inden-1-yl)oxy)phenoxy)-methyl) nicotinonitrile (220 mg, 0.41 mmol) and potassium phosphate (200 mg, 0.94 mmol) in THF (4 mL) and water (1 mL) at room temperature. The vial was sealed and the resultant suspension was stirred for 16 h before it was diluted with ethyl acetate and water. The aqueous layer was separated, and extracted once more with ethyl acetate before the combined organic extract was washed with brine, dried over magnesium sulfate, filtered and concentrated. The crude product was taken up in a small amount of dichloromethane and charged to a RediSepRf normal phase silica gel Teledyne ISCO 12 g disposable column which was first eluted with dichloromethane for 30 mL, followed by 0-20% B for 240 mL and finally 20-100% B for 200 mL where solvent A=dichloromethane and solvent B=methanol. Fractions containing the desired product were combined and dried via centrifugal evaporation to afford the product, 5-((4-chloro-5-((4-(2-chloro-3-(3-(((S)-2,3-dihydroxypropyl)amino)propoxy)phenyl)-2,3-dihydro-1H-inden-1-yl) oxy)-2-formylphenoxy)methyl)nicotinonitrile (117.7 mg, 47.1%), as a orange solid. This material was carried forward directly and used 'as is'.

LCMS: $t_R$=1.26 min; LCMS (ESI) m/z=662.10 and 664.05 [M+H]$^+$. LCMS conditions: Injection Vol=1 µL; Gradient=2-98% B; Gradient Time=1.5 min; Flow Rate=0.8 ml/min; Wavelength=220 nm; Mobile Phase A=0:100 acetonitrile:water with 0.05% trifluoroacetic acid; Mobile Phase B=100:0 acetonitrile:water with 0.05% trifluoroacetic acid; Column=Waters Aquity BEH C18, 2.1×50 mm, 1.7 U; Oven Temp=40° C.

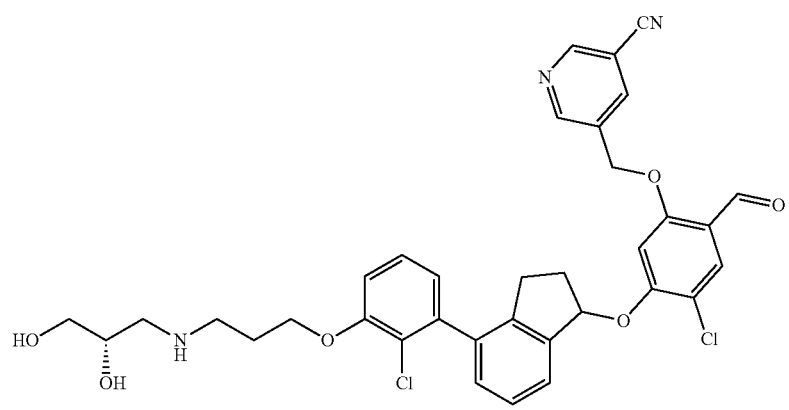 [SMILES: N#Cc1cncc(COc2cc(OC3CCc4c(-c5cccc(OCCCNC[C@H](O)CO)c5Cl)cccc43)c(Cl)cc2C=O)c1]

Example 1019: (2R)-2-((5-chloro-4-((4-(2-chloro-3-(3-(((S)-2,3-dihydroxypropyl)amino)propoxy)phenyl)-2,3-dihydro-1H-inden-1-yl)oxy)-2-((5-cyanopyridin-3-yl)methoxy)benzyl)amino)-3-hydroxy-2-methylpropanoic acid

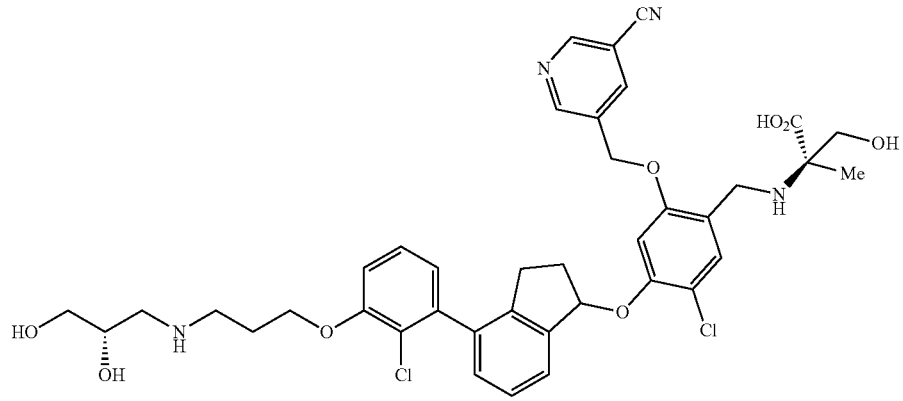 [SMILES: C[C@](CO)(NCc1cc(Cl)c(OC2CCc3c(-c4cccc(OCCCNC[C@H](O)CO)c4Cl)cccc32)cc1OCc1cncc(C#N)c1)C(=O)O]

1 M Sodium cyanotrihydroborate (0.90 µL, 0.090 mmol) was added portionwise after 3 h to a stirred solution of 5-((4-chloro-5-((4-(2-chloro-3-(3-(((S)-2,3-dihydroxypropyl)amino)propoxy)phenyl)-2,3-dihydro-1H-inden-1-yl)oxy)-2-formylphenoxy)-methyl)nicotinonitrile (30.0 mg, 0.045 mmol), (R)-2-amino-3-hydroxy-2-methylpropanoic acid (10.8 mg, 0.091 mmol), acetic acid (13 µL, 0.23 mmol), and 4 Å powdered molecular sieves (25 mg) in dry DIVIF (0.50 mL) and MeOH (0.42 mL) at room temperature. The mixture was stirred at room temperature for 16 h before it was diluted with DIVIF and MeOH (1:2) up to 2 mL total volume, filtered through a syringe filter and purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 7-47% B over 20 min, then a 5 min hold at 100% B; Flow Rate: 20 mL/min; Column Temperature: 25° C. Fraction collection was triggered by MS and UV signals. Fractions containing the desired product were combined and dried via centrifugal evaporation. The yield of the product was 10.4 mg (30.0%), and its estimated purity by LCMS analysis was 100%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 100.0%; Observed Mass: 765.16; Retention Time: 1.64 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 100.0%; Observed Mass: 765.17; Retention Time: 1.61 min.

Example 1020: 5-((4-Chloro-5-((4-(2-chloro-3-(3-(((S)-2,3-dihydroxypropyl)amino)propoxy)phenyl)-2,3-dihydro-1H-inden-1-yl)oxy)-2-(hydroxymethyl)phenoxy)methyl)nicotinonitrile

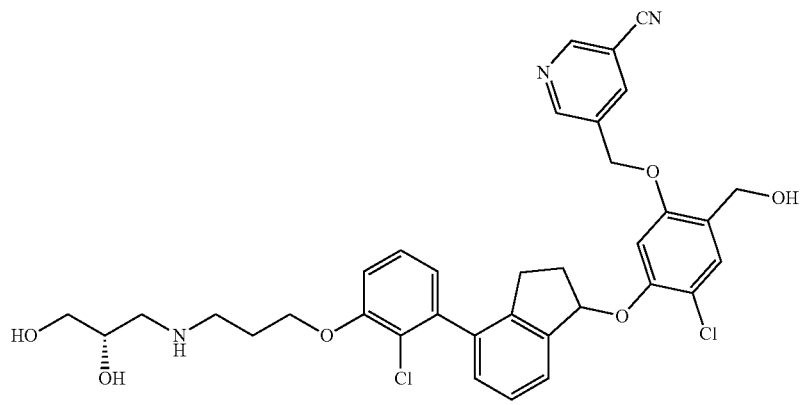 [SMILES: N#Cc1cncc(COc2cc(OC3CCc4c(-c5cccc(OCCCNC[C@H](O)CO)c5Cl)cccc43)c(Cl)cc2CO)c1]

Example 1020 was isolated from the purification of the reaction mixture for Example 1019 above. The yield of the product was 4.7 mg (14.0%), and its estimated purity by LCMS analysis was 90%. Analytical LCMS was used to determine the final purity. Injection 1 conditions: Column:

Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 92.4%; Observed Mass: 664.09; Retention Time: 1.9 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 89.8%; Observed Mass: 664.07; Retention Time: 1.87 min.

Example 1021: (5-Chloro-4-((4-(2-chloro-3-(3-(((S)-2,3-dihydroxypropyl)amino)propoxy)phenyl)-2,3-dihydro-1H-inden-1-yl)oxy)-2-((5-cyanopyridin-3-yl)methoxy)benzyl)-L-homoserine tions containing the desired product were combined and dried via centrifugal evaporation. The yield of the product was 2.1 mg (5.9%), and its estimated purity by LCMS analysis was 97%. Analytical LCMS was used to determine the final purity. Injection 1 conditions: Column: Waters XBridge C18, 2.1×50 mm, 1.7 U; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.50 min hold at 100% B; Flow: 1 mL/min; Detection: MS and UV (220 nm). Injection 1 results: Purity: 98.5%; Observed Mass: 765.18; Retention Time: 1.5 min. Injection 2 conditions: Column: Waters XBridge C18, 2.1×50 mm, 1.7 U; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 min, then a 0.50 min hold at 100% B; Flow: 1 mL/min; Detection: MS and UV (220 nm). Injection 2 results: Purity: 97.1%; Observed Mass: 765.2; Retention Time: 1.41 min.

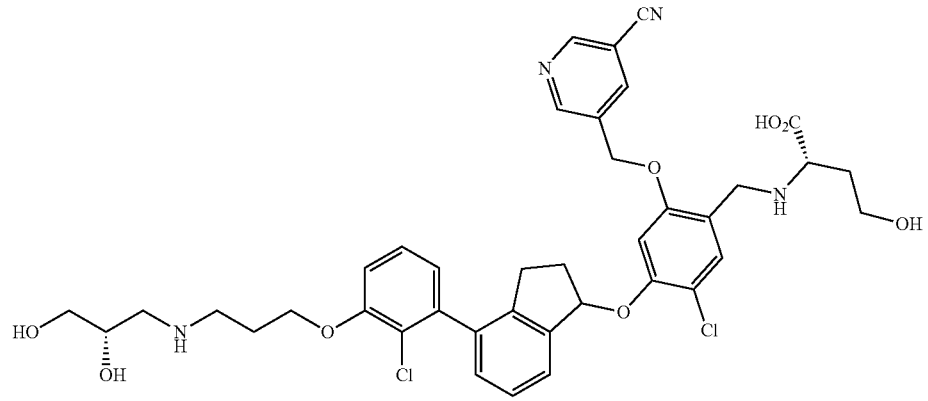 [SMILES: N#Cc1cncc(COc2cc(OC3CCc4c(-c5cccc(OCCCNC[C@H](O)CO)c5Cl)cccc43)c(Cl)cc2CN[C@@H](CCO)C(=O)O)c1]

Borane•2-picoline complex (9.7 mg, 0.091 mmol) was added in one portion after 3 h to a stirred solution of 5-((4-chloro-5-((4-(2-chloro-3-(3-(((S)-2,3-dihydroxypropyl)-amino)propoxy)phenyl)-2,3-dihydro-1H-inden-1-yl)oxy)-2-formylphenoxy)methyl)-nicotinonitrile (30.0 mg, 0.045 mmol), L-homoserine (53.9 mg, 0.453 mmol), acetic acid (26 μL, 0.45 mmol), and 4A powdered molecular sieves (25 mg) in dry DMF (0.50 mL) at room temperature. The mixture was stirred for 16 h before it was diluted with DMF and MeOH (1:2) up to 2 mL total volume, filtered through a syringe filter and purified via preparative LCMS with the following conditions: Column: XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 3-43% B over 23 min, then a 5 min hold at 100% B; Flow Rate: 20 mL/min; Column Temperature: 25° C. Fraction collection was triggered by UV signals. Fractions containing the desired product were combined and dried via centrifugal evaporation. This material was further purified via preparative LCMS with the following conditions: Column:) XBridge C18, 19×200 mm, 5 U; Mobile Phase A: 5:95 acetonitrile:water with 10 mM ammonium acetate; Mobile Phase B: 95:5 acetonitrile:water with 10 mM ammonium acetate; Gradient: 9-49% B over 25 min, then a 5 min hold at 100% B; Flow Rate: 20 mL/min; Column Temperature: 25° C. Fraction collection was triggered by MS and UV signals. Frac- Biological Assay The ability of the compounds of formula (I) to bind to PD-L1 was investigated using a PD-1/PD-L1 Homogenous Time-Resolved Fluorescence (HTRF) binding assay.
Homogenous Time-Resolved Fluorescence (HTRF) binding assay.

The interaction of PD-1 and PD-L1 can be assessed using soluble, purified preparations of the extracellular domains of the two proteins. The PD-1 and PD-L1 protein extracellular domains were expressed as fusion proteins with detection tags, for PD-1, the tag was the Fc portion of Immunoglobulin (PD-1-Ig) and for PD-L1 it was the 6 histidine motif (PD-L1-His). All binding studies were performed in an HTRF assay buffer consisting of dPBS supplemented with 0.1% (with) bovine serum albumin and 0.05% (v/v) Tween-20. For the h/PD-L1-His binding assay, inhibitors were pre-incubated with PD-L1-His (10 nM final) for 15m in 4 μl of assay buffer, followed by addition of PD-1-Ig (20 nM final) in 1 μl of assay buffer and further incubation for 15m. HTRF detection was achieved using europium crypate-labeled anti-Ig (1 nM final) and allophycocyanin (APC) labeled anti-His (20 nM final). Antibodies were diluted in HTRF detection buffer and 5 μl was dispensed on top of the binding reaction. The reaction mixture was allowed to equilibrate for 30 minutes and the resulting signal (665 nm/620 nm ratio) was obtained using an EnVision fluorometer. Additional binding assays were established between the human proteins PD-1-Ig/PD-L2-His (20 & 5 nM, respectively) and CD8O-His/PD-L1-Ig (100 & 10 nM, respectively).

Recombinant Proteins: Human PD-1 (25-167) with a C-terminal human Fc domain of immunoglobulin G (Ig) epitope tag [hPD-1 (25-167)-3S-IG] and human PD-L1 (18-239) with a C-terminal His epitope tag [hPD-L1(18-239)-TVMV-His] were expressed in HEK293T cells and purified sequentially by ProteinA affinity chromatography and size exclusion chromatography. Human PD-L2-His and CD8O-His was obtained through commercial sources.

```
           Sequence of recombinant human PD-1-Ig hPD1(25-167)-3S-IG
  1  LDSPDRPWNP PTFSPALLVV TEGDNATFTC SFSNTSESFV LNWYRMSPSN

51  QTDKLAAPPE DRSQPGQDCR FRVTQLPNGR DFHMSVVRAR RNDSGTYLCG

101  AISLAPKAQI KESLRAELRV TERRAEVPTA HPSPSPRPAG QFQGSPGGGG

151  GREPKSSDKT HTSPPSPAPE LLGGSSVFLF PPKPKDTLMI SRDELTKNQV

201  VDVSHEDPEV KFNWYVDGVE VHNAKTKPRE EQYNSTYRVV SVLTVLHQDW

251  LNGKEYKCKV SNKALPAPIE KTISKAKGQP REPQVYTLPP SRDELTKNQV

300  SLTCLVKGFY PSDIAVEWES NGQPENNYKT TPPVLDSDGS FFLYSKLTVD

351  KSRWQQGNVF SCSVMHEALH NHYTQKSLSL SPGK (SEQ ID NO: 1)

Sequence of recombinant human PD-L1-His hPDL1(18-239)-TVMV-His
  1  AFTVTVPKDL YVVEYGSNMT IECKFPVEKQ LDLAALIVYW EMEDKNIIQF

51  VHGEEDLKVQ HSSYRQRARL LKDQLSLGNA ALQITDVKLQ DAGVYRCMIS

101  YGGADYKRIT VKVNAPYNKI NQRILVVDPV TSEHELTCQA EGYPKAEVIW

151  TSSDHQVLSG KTTTTNSKRE EKLFNVTSTL RINTTTNEIF YCTFRRLDPE

201  ENHTAELVIP ELPLAHPPNE RTGSSETVRF QGHHHHHH (SEQ ID NO: 2)
```

The table below lists the $IC_{50}$ values for representative examples of this disclosure measured in the PD-1/PD-L1 Homogenous Time-Resolved Fluorescence (HTRF) binding assay.

| Example Number | IC50 (µM) |
|---|---|
| Example 1001 | 0.0014 |
| Example 1002 | 0.0009 |
| Example 1003 | 0.0091 |
| Example 1004 | 0.0039 |
| Example 1005 | 0.0106 |
| Example 1006 | 0.0035 |
| Example 1007 | 0.0043 |
| Example 1008 | 0.0030 |
| Example 1009 | 0.0241 |
| Example 1010 | 0.0020 |
| Example 1011 | 0.0104 |
| Example 1012 | 0.0018 |
| Example 1013 | 0.0181 |
| Example 1014 | 0.0058 |
| Example 1015 | 0.0019 |
| Example 1016 | 0.0034 |
| Example 1017 | 0.0002 |
| Example 1018 | 0.0029 |
| Example 1019 | 0.0025 |
| Example 1020 | 0.0109 |
| Example 1021 | 0.0010 |

The compounds of formula (I) possess activity as inhibitors of the PD-1/PD-L1 interaction, and therefore, may be used in the treatment of diseases or deficiencies associated with the PD-1/PD-L1 interaction. Via inhibition of the PD-1/PD-L1 interaction, the compounds of the present disclosure may be employed to treat infectious diseases such as HIV, septic shock, Hepatitis A, B, C, or D and cancer.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All publications, patents, and patent applications disclosed herein are incorporated by reference to the same extent as if each individual publication, patent or patent application was specifically and individually indicated to be incorporated by reference.

What is claimed is:

1. A compound of formula (I):

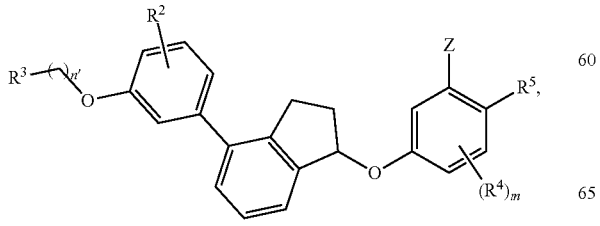

(I)

or a pharmaceutically acceptable salt thereof, wherein:

m is 0, 1, or 2;

n' is 1, 2, or 3;

Z is selected from hydrogen, —CH$_3$, —O(CH$_2$)$_n$X and —O(CH$_2$)$_m$Ar; wherein n is 1, 2, 3, or 4;

X is selected from hydrogen, —CH$_3$, —CF$_3$, CN, —CO$_2$R$^1$, —C(O)NH2, OR$^1$, and pyrrolidonyl;

R$^1$ is H or C$_1$-C$_3$alkyl, provided that when n is 1, R$^1$ is C$_1$-C$_3$alkyl;

Ar is selected from benzodioxanyl, indazolyl, isoquinolinyl, isoxazolyl, naphthyl, oxadiazolyl, phenyl, pyridinyl, pyrimidinyl, and quinolinyl; wherein each ring is optionally substituted with 1, 2, 3, or 4 substituents independently selected from $C_1$-$C_4$alkoxy, $C_1$-$C_4$alkoxycarbonyl, $C_1$-$C_4$alkoxycarbonylamino, $C_1$-$C_4$alkyl, ($C_1$-$C_4$alkyl)carbonyl, ($C_1$-$C_4$alkyl)sulfonyl, amido, aminocarbonyl, aminocarbonyl($C_1$-$C_3$alkyl), —$(CH_2)_g CO_2 C_1$-$C_4$alkyl, —$(CH_2)_q$OH, carboxy, cyano, formyl, halo, halo$C_1$-$C_4$alkyl, halo$C_1$-$C_4$alkoxy, nitro, phenyl optionally substituted with one cyano group, phenyloxy optionally substituted with one halo group, phenylcarbonyl, pyrrole, and tetrahydropyran; and wherein q is 0, 1, 2, 3, or 4;

$R^2$ is selected from hydrogen, $C_1$-$C_3$alkyl, cyano, halo, and halo$C_1$-$C_3$alkyl;

$R^3$ is

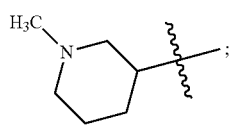 [SMILES: *C1CCCN(C)C1]

each $R^4$ is independently selected from $C_2$-$C_4$alkenyl, $C_1$-$C_4$alkoxy, $C_1$-$C_4$alkyl, cyano, halo, and halo$C_1$-$C_4$alkyl; and $R^5$ is selected from —$(CH_2)_p$CHO, —$(CH_2)_p CO_2 H$, —$(CH_2)_w$OH, —$C(O)NR^{100}R^{101}$, —$CH(CH_3)NR^q R^8$, and —$(CH_2)_w NR^q R^8$; wherein $R^{100}$ and $R^{101}$ are selected from hydrogen, $C_1$-$C_6$alkyl, and hydroxy($C_1$-$C_6$alkyl) optionally substituted with an additional hydroxy group; or, $R^{100}$ and $R^{101}$, together with the nitrogen atom to which they are attached, form a six-membered ring optionally substituted with a carboxy group;

p is 0, 1, 2, or 3;

w is 1, 2, 3, or 4;

$R^q$ is selected from hydrogen, $C_1$-$C_4$alkyl, benzyl, ($C_3$-$C_6$cycloalkyl)$C_1$-$C_3$alkyl, halo$C_1$-$C_4$alkyl, hydroxy$C_1$-$C_6$alkyl optionally substituted with a second hydroxy group, and pyridinyl($C_1$-$C_3$alkyl) optionally substituted with a cyano group; and $R^8$ is selected from hydrogen, $C_1$-$C_4$alkyl, —$(CH_2)_n N(CH_3)_2$, carboxy$C_2$-$C_6$alkenyl, carboxy$C_1$-$C_6$alkyl, and hydroxy$C_1$-$C_6$alkyl, wherein the alkyl part of the carboxy$C_1$-$C_6$alkyl and the hydroxy$C_1$-$C_6$alkyl is optionally substituted with one hydroxy or phenyl group wherein the phenyl group is further optionally substituted with a hydroxy group;

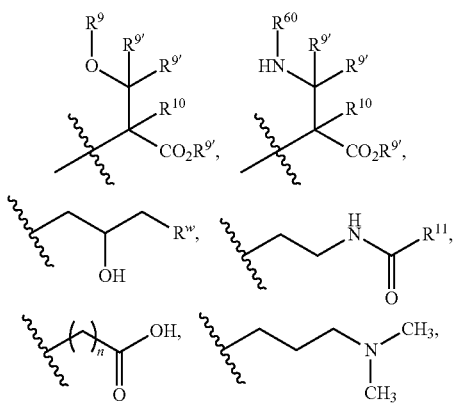

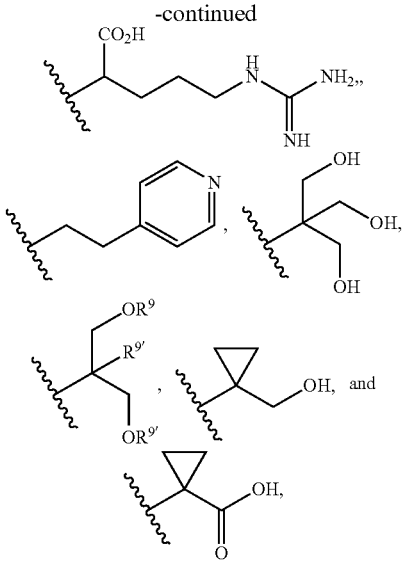

and $R^w$ is —$CONH_2$, $R^9$ is selected from hydrogen, benzyl, and methyl;

each $R^{9'}$ is independently selected from hydrogen and $C_1$-$C_3$alkyl;

$R^{10}$ is selected from hydrogen, $C_1$-$C_3$alkyl, and benzyl;

$R^{11}$ is selected from $C_2$-$C_4$alkenyl and $C_1$-$C_4$alkyl; and $R^{60}$ is selected from hydrogen, $C_1$-$C_6$alkyl, and $C_1$-$C_6$alkoxycarbonyl, or $R^8$ and $R^q$, together with the nitrogen atom to which they are attached, form a ring selected from

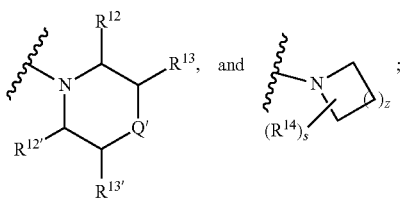

wherein s is 0, 1, or 2;

z is 1, 2, or 3;

Q' is selected from CHR$^{13''}$, S, O, NH, NC(O)OC$_1$-$C_6$alkyl, N(CH$_2$)$_2$OH, and NCH$_3$;

$R^{12}$ and $R^{12'}$ are independently selected from hydrogen, —$CO_2 H$, hydroxy$C_1$-$C_4$alkyl, oxo, and —C(O)NHSO$_2 R^{16}$;

$R^{13}$ and $R^{13'}$ are independently selected from hydrogen, hydroxy$C_1$-$C_4$alkyl, oxo, and —$CO_2 H$;

$R^{13''}$ is selected from hydroxy$C_1$-$C_3$alkyl, and —$CO_2 H$;

each $R^{14}$ is independently selected from $C_1$-$C_4$alkoxycarbonyl, $C_1$-$C_6$alkyl, carboxy, halo, hydroxy, hydroxy$C_1$-$C_4$alkyl, —NR$^c R^d$, and phenyloxycarbonyl wherein the phenyl is optionally substituted with a nitro group, wherein R$^{c'}$ and R$^{d'}$ are independently selected from hydrogen, $C_1$-$C_4$alkoxycarbonyl, and $C_1$-$C_4$alkylcarbonyl; and $R^{16}$ is selected from trifluoromethyl, cyclopropyl, $C_1$-$C_4$alkyl, dimethylamino, and imidazolyl substituted with a methyl group.

2. A compound of claim 1, or a pharmaceutically acceptable salt thereof, wherein $R^2$ is halo.

3. A compound of claim 1, or a pharmaceutically acceptable salt thereof, wherein Z is —O(CH$_2$)$_n$Ar wherein n is 1 and Ar is pyridinyl substituted with one cyano group.

4. A compound of claim 1, or a pharmaceutically acceptable salt thereof, wherein m is 1 and $R^4$ is halo.

5. A compound of claim 1, or a pharmaceutically acceptable salt thereof, wherein $R^5$ is

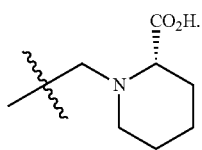 [SMILES: *CN1CCCC[C@H]1C(=O)O]

6. A compound of claim 1, or a pharmaceutically acceptable salt thereof, wherein $R^5$ is

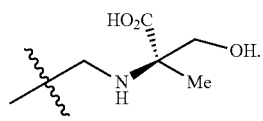 [SMILES: *CN[C@](C)(CO)C(=O)O]

7. A compound of claim 1, or a pharmaceutically acceptable salt thereof, wherein $R^5$ is —CH$_2$OH.

8. A compound of claim 1, or a pharmaceutically acceptable salt thereof, wherein $R^5$ is

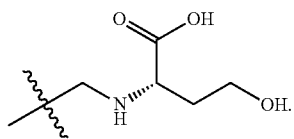 [SMILES: *CN[C@@H](CCO)C(=O)O]

9. A compound of claim 1, or a pharmaceutically acceptable salt thereof, wherein:

Z is —O(CH$_2$)$_n$Ar wherein n is 1 and Ar is pyridinyl substituted with one cyano group;

$R^2$ is halo;

m is 1;

$R^4$ is halo; and $R^5$ is selected from

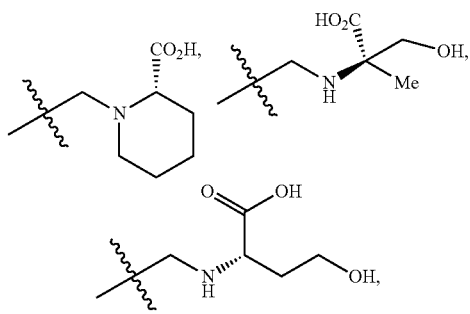

and —CH$_2$OH.

10. A compound selected from (2S)-1-(5-chloro-4-((4-(2-chloro-3-((1-methylpiperidin-3-yl)methoxy)phenyl)-2,3-dihydro-1H-inden-1-yl)oxy)-2-((5-cyanopyridin-3-yl)methoxy)benzyl)piperidine-2-carboxylic acid;

(2R)-2-((5-chloro-4-((4-(2-chloro-3-((1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid;

5-((4-chloro-5-((4-(2-chloro-3-((1-methylpiperidin-3-yl)methoxy)phenyl)-2,3-dihydro-1H-inden-1-yl)oxy)-2-(hydroxymethyl)phenoxy)-methyl)nicotinonitrile;

((R)-2-((5-chloro-4-(((S)-4-(2-chloro-3-(((R)-1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid;

5-((4-chloro-5-(((S)-4-(2-chloro-3-(((R)-1-methylpiperidin-3-yl)methoxy)phenyl)-2,3-dihydro-1H-inden-1-yl)oxy)-2-(hydroxymethyl)phenoxy)methyl)nicotinonitrile;

(R)-2-((5-chloro-4-(((R)-4-(2-chloro-3-(((R)-1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid;

5-((4-chloro-5-(((R)-4-(2-chloro-3-(((R)-1-methylpiperidin-3-yl)methoxy)phenyl)-2,3-dihydro-1H-inden-1-yl)oxy)-2-(hydroxymethyl)phenoxy)methyl)nicotinonitrile;

(R)-2-((5-chloro-4-(((S)-4-(2-chloro-3-(((S)-1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid;

5-((4-chloro-5-(((S)-4-(2-chloro-3-(((S)-1-methylpiperidin-3-yl)methoxy)phenyl)-2,3-dihydro-1H-inden-1-yl)oxy)-2-(hydroxymethyl)phenoxy)methyl)nicotinonitrile;

(R)-2-((5-chloro-4-(((R)-4-(2-chloro-3-(((S)-1-methylpiperidin-3-yl)methoxy)phenyl)-2,3-dihydro-1H-inden-1-yl)oxy)-2-((5-cyanopyridin-3-yl)methoxy)benzyl)amino)-3-hydroxy-2-methylpropanoic acid;

5-((4-chloro-5-(((R)-4-(2-chloro-3-(((S)-1-methylpiperidin-3-yl)methoxy)phenyl)-2,3-dihydro-1H-inden-1-yl)oxy)-2-(hydroxymethyl)phenoxy)methyl)nicotinonitrile;

(2R)-2-((5-chloro-2-((5-cyanopyridin-3-yl)methoxy)-4-((4-(3-(3-((R)-3-hydroxypyrrolidin-1-yl)propoxy)-2-methylphenyl)-2,3-dihydro-1H-inden-1-yl)oxy)benzyl)-amino)-3-hydroxy-2-methylpropanoic acid;

5-((4-chloro-2-(hydroxymethyl)-5-((4-(3-(3-((R)-3-hydroxypyrrolidin-1-yl)propoxy)-2-methylphenyl)-2,3-dihydro-1H-inden-1-yl)oxy)phenoxy)methyl)nicotinonitrile;

(2S)-1-(5-chloro-2-((5-cyanopyridin-3-yl)methoxy)-4-((4-(3-(3-((R)-3-hydroxypyrrolidin-1-yl)propoxy)-2-methylphenyl)-2,3-dihydro-1H-inden-1-yl)oxy)benzyl)-piperidine-2-carboxylic acid;

(5-chloro-2-((5-cyanopyridin-3-yl)methoxy)-4-((4-(3-(3-((R)-3-hydroxypyrrolidin-1-yl)propoxy)-2-methylphenyl)-2,3-dihydro-1H-inden-1-yl)oxy)benzyl)-L-homoserine;

(2R)-2-((4-((4-(3-(3-(4-acetamidopiperidin-1-yl)propoxy)-2-chlorophenyl)-2,3-dihydro-1H-inden-1-yl)oxy)-5-chloro-2-((5-cyanopyridin-3-yl)methoxy)benzyl)amino)-3-hydroxy-2-methylpropanoic acid;

(2S)-1-(4-((4-(3-(3-(4-acetamidopiperidin-1-yl)propoxy)-2-chlorophenyl)-2,3-dihydro-1H-inden-1-yl)oxy)-5-chloro-2-((5-cyanopyridin-3-yl)methoxy)benzyl)piperidine-2-carboxylic acid;

(4-((4-(3-(3-(4-acetamidopiperidin-1-yl)propoxy)-2-chlorophenyl)-2,3-dihydro-1H-inden-1-yl)oxy)-5-chloro-2-((5-cyanopyridin-3-yl)methoxy)benzyl)-L-homoserine;

(2R)-2-((5-chloro-4-((4-(2-chloro-3-(3-(((S)-2,3-dihydroxypropyl)amino)propoxy)phenyl)-2,3-dihydro-1H-inden-1-yl)oxy)-2-((5-cyanopyridin-3-yl)methoxy)benzyl)amino)-3-hydroxy-2-methylpropanoic acid;

5-((4-chloro-5-((4-(2-chloro-3-(3-(((S)-2,3-dihydroxypropyl)amino)propoxy)phenyl)-2,3-dihydro-1H-inden-1-yl)oxy)-2-(hydroxymethyl)phenoxy)methyl)nicotinonitrile; and (5-chloro-4-((4-(2-chloro-3-(3-(((S)-2,3-dihydroxypropyl)amino)propoxy)phenyl)-2,3-dihydro-1H-inden-1-yl)oxy)-2-((5-cyanopyridin-3-yl)methoxy)benzyl)-L-homoserine;

or a pharmaceutically acceptable salt thereof.

11. A pharmaceutical composition comprising a compound of claim 1, or a pharmaceutically acceptable salt thereof, and a pharmaceutically acceptable carrier.

12. A method of enhancing, stimulating, modulating and/or increasing an immune response in a subject in need thereof, said method comprising administering to the subject a therapeutically effective amount of a compound of claim 1, or a pharmaceutically acceptable salt thereof.

13. A method of inhibiting growth, proliferation, or metastasis of cancer cells in a subject in need thereof, said method comprising administering to the subject a therapeutically effective amount of a compound of claim 1, or a pharmaceutically acceptable salt.

* * * * *

UNITED STATES PATENT AND TRADEMARK OFFICE
CERTIFICATE OF CORRECTION

PATENT NO. : 11,578,054 B2
APPLICATION NO. : 16/977374
DATED : February 14, 2023
INVENTOR(S) : Kap-Sun Yeung et al.

Page 1 of 1

It is certified that error appears in the above-identified patent and that said Letters Patent is hereby corrected as shown below:

In the Claims

Column 64
Claim 1, Line 57, "—O(CH$_2$)$_m$Ar;" should read -- —O(CH$_2$)$_n$Ar; --; and
Claim 1, Line 60, "—C(O)NH2" should read -- —C(O)NH$_2$, --.

Column 65
Claim 1, Line 4, "—(CH$_2$)$_g$" should read -- —(CH$_2$)$_q$ --.

Column 66
Claim 1, Line 12-17, " 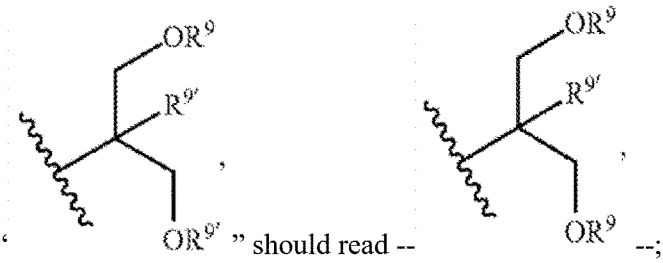 " should read --
Claim 1, Line 49, "0," should read -- O, --; and
Claim 1, Line 57, "R$^{13}$"is" should read -- R$^{13}$ is --.

Signed and Sealed this
Second Day of May, 2023

Katherine Kelly Vidal
*Director of the United States Patent and Trademark Office*